United States Patent
Browd et al.

(10) Patent No.: US 9,662,478 B2
(45) Date of Patent: May 30, 2017

(54) BODY FLUID DRAINAGE SYSTEM

(75) Inventors: Samuel R. Browd, Seattle, WA (US); Barry R. Lutz, Seattle, WA (US)

(73) Assignee: University of Washington, Seattle, WA (US)

(*) Notice: Subject to any disclaimer, the term of this patent is extended or adjusted under 35 U.S.C. 154(b) by 654 days.

(21) Appl. No.: 13/636,115

(22) PCT Filed: Mar. 21, 2011

(86) PCT No.: PCT/US2011/029261
§ 371 (c)(1),
(2), (4) Date: Nov. 8, 2012

(87) PCT Pub. No.: WO2011/116393
PCT Pub. Date: Sep. 22, 2011

(65) Prior Publication Data
US 2013/0197422 A1   Aug. 1, 2013

Related U.S. Application Data

(60) Provisional application No. 61/315,660, filed on Mar. 19, 2010, provisional application No. 61/407,359, filed on Oct. 27, 2010.

(51) Int. Cl.
*A61M 5/00* (2006.01)
*A61M 27/00* (2006.01)
(Continued)

(52) U.S. Cl.
CPC .......... *A61M 27/006* (2013.01); *A61B 5/031* (2013.01); *A61M 39/28* (2013.01); *A61B 5/0215* (2013.01); *A61M 2025/0003* (2013.01)

(58) Field of Classification Search
CPC ........ A61M 27/006; A61M 2025/0002; A61M 2205/3344; A61M 2025/0003; A61B 5/03; A61B 5/031
(Continued)

(56) References Cited

U.S. PATENT DOCUMENTS 3,589,363 A * 6/1971 Banko et al. .................. 604/22
3,769,982 A   11/1973 Schulte
(Continued)

FOREIGN PATENT DOCUMENTS

CN    2421023 Y    2/2001
CN    2614684 Y    5/2004
(Continued)

OTHER PUBLICATIONS

Bondurant, C.P. and D.F. Jimenez, Epidemiology of cerebrospinal fluid shunting. Pediatr Neurosurg, 1995. 23(5): p. 254-8; discussion 259.
(Continued)

*Primary Examiner* — Tatyana Zalukaeva
*Assistant Examiner* — Ariana Zimbouski
(74) *Attorney, Agent, or Firm* — Perkins Coie LLP

(57) ABSTRACT

Drainage systems for excess body fluids and associated methods are disclosed herein. A body fluid drainage system in accordance with an embodiment of the present technology, for example, can include a catheter that has an exterior surface, a proximal portion, and a distal portion opposite the proximal portion. The body fluid drainage system can further include a valve device, a pressure sensor, and a controller operatively coupled to the valve device and the pressure sensor. The valve device can include an actuator positioned over the exterior surface of the catheter. The actuator is movable between an open position that allows body fluid flow through the catheter, a closed position that at least substantially obstructs the body fluid flow through the catheter, and intermediate positions that partially obstruct the body fluid flow through the catheter. The controller can change the position of the actuator in response to a predetermined condition of the pressure sensor.

45 Claims, 12 Drawing Sheets

(51) Int. Cl.
  *A61B 5/03* (2006.01)
  *A61M 39/28* (2006.01)
  *A61B 5/0215* (2006.01)
  *A61M 25/00* (2006.01)

(58) Field of Classification Search
  USPC .......................................................... 604/9
  See application file for complete search history.

(56) References Cited

U.S. PATENT DOCUMENTS

| | | | |
|---|---|---|---|
| 3,911,902 A | 10/1975 | Delpy | |
| 3,913,882 A | 10/1975 | Moulet et al. | |
| 3,991,768 A | 11/1976 | Portnoy | |
| 4,156,422 A | 5/1979 | Hildebrandt et al. | |
| 4,741,730 A | 5/1988 | Dormandy, Jr. et al. | |
| 5,573,007 A * | 11/1996 | Bobo, Sr. ............ | A61B 5/0215 600/561 |
| 5,584,314 A | 12/1996 | Bron et al. | |
| 6,241,660 B1 | 6/2001 | Dolle et al. | |
| 6,264,625 B1 | 7/2001 | Rubenstein et al. | |
| 6,295,877 B1 | 10/2001 | Aboul-Hosn | |
| 6,336,924 B1 * | 1/2002 | Lecuyer et al. ............. | 604/540 |
| 6,383,160 B1 | 5/2002 | Madsen | |
| 6,585,677 B2 | 7/2003 | Cowan et al. | |
| 6,673,022 B1 * | 1/2004 | Bobo et al. .................. | 600/561 |
| 6,953,444 B2 | 10/2005 | Rosenberg | |
| 7,189,221 B2 | 3/2007 | Silverberg et al. | |
| 7,309,330 B2 | 12/2007 | Bertrand et al. | |
| 8,066,681 B1 | 11/2011 | Hall et al. | |
| 8,109,899 B2 | 2/2012 | Sundstrom et al. | |
| 8,123,714 B2 | 2/2012 | Ludin et al. | |
| 8,192,366 B2 | 6/2012 | Mauge et al. | |
| 8,870,787 B2 * | 10/2014 | Yadav et al. .................. | 600/561 |
| 2003/0139699 A1 | 7/2003 | Rosenberg | |
| 2003/0233143 A1 | 12/2003 | Gharib et al. | |
| 2004/0111079 A1 | 6/2004 | Hayes et al. | |
| 2004/0260229 A1 * | 12/2004 | Meir ................ | 604/9 |
| 2005/0010159 A1 | 1/2005 | Reich et al. | |
| 2005/0020962 A1 | 1/2005 | Reich et al. | |
| 2005/0055009 A1 * | 3/2005 | Rosenberg .................... | 604/500 |
| 2005/0182463 A1 | 8/2005 | Hunter et al. | |
| 2005/0187515 A1 | 8/2005 | Varrichio et al. | |
| 2006/0052737 A1 * | 3/2006 | Bertrand et al. .................. | 604/9 |
| 2007/0038171 A1 | 2/2007 | Mayer et al. | |
| 2007/0213656 A1 | 9/2007 | Ferdinand | |
| 2009/0005720 A1 * | 1/2009 | Ludin et al. ...................... | 604/9 |
| 2010/0076366 A1 * | 3/2010 | Henderson et al. ............. | 604/9 |
| 2010/0113967 A1 * | 5/2010 | Bobo, Sr. ............ | A61M 25/003 600/561 |
| 2010/0121250 A1 | 5/2010 | Pizzi et al. | |
| 2010/0298771 A1 | 11/2010 | Tan | |
| 2010/0331813 A1 | 12/2010 | Robinson et al. | |
| 2011/0029050 A1 | 2/2011 | Elefteriades et al. | |
| 2011/0166497 A1 * | 7/2011 | Criado et al. .................... | 604/9 |
| 2011/0275976 A1 | 11/2011 | Negre et al. | |
| 2012/0046596 A1 | 2/2012 | Ludin et al. | |
| 2012/0259265 A1 | 10/2012 | Salehi et al. | |
| 2013/0197422 A1 | 8/2013 | Browd et al. | |
| 2013/0247644 A1 | 9/2013 | Swoboda et al. | |

FOREIGN PATENT DOCUMENTS

| | | |
|---|---|---|
| CN | 1565662 A | 1/2005 |
| CN | 101342402 A | 1/2009 |
| DE | 4130601 A1 | 4/1992 |
| EP | 0982048 A1 | 3/2000 |
| EP | 1512428 A1 | 3/2005 |
| WO | 0203860 A1 | 1/2002 |

OTHER PUBLICATIONS

Browd, S.R., et al., Failure of cerebrospinal fluid shunts: part II: overdrainage, loculation, and abdominal complications. Pediatr Neurol, 2006. 34(3): p. 171-6.
Association, H., Learning about hydrocephalus. 2009.
Drake, J.M., J.R. Kestle, and S. Tuli, Cerebrospinal fluid shunt technology. Clin Neurosurg, 2000. 47: p. 336-45.
Drake, J.M., J.R. Kestle, and S. Tuli, CSF shunts 50 years on—past, present and future. Childs Nerv Syst, 2000. 16(10-11): p. 800-4.
Drake, J.M. and J.T. Kestle, Determining the best cerebrospinal fluid shunt valve design: the pediatric valve design trial. Neurosurgery, 1998. 43(5): p. 1259-60.
Epstein, F., How to keep shunts functioning, or "The impossible dream". Clin Neurosurg, 1985.32: p. 608-31.
Kestle, J., R. Milner, and J. Drake, The shunt design trial: variation in surgical experience did not influence shunt survival. Pediatr Neurosurg, 1999. 30(6): p. 283-7.
Kestle, J.R., et al., Lack of benefit of endoscopic ventriculoperitoneal shunt insertion: a multicenter randomized trial. J Neurosurg, 2003. 98(2): p. 284-90.
Williams, M.A., et al., Priorities for hydrocephalus research: report from a National Institutes of Health-sponsored workshop. J Neurosurg, 2007. 107(5 Suppl): p. 345-57.
Kestle, J., et al., Long-term follow-up data from the Shunt Design Trial. Pediatr Neurosurg, 2000. 33(5): p. 230-236.
Simon, T.D., et al., Infection rates following initial cerebrospinal fluid shunt placement across pediatric hospitals in the United States. Clinical article. J Neurosurg Pediatr, 2009.4(2): p. 156-65.
National Center for Health Statistics. Birth Data. National Vital Statistics System. [Online] [Cited: Aug. 26, 2010] http://www.cdc.gov/nchs/births.htm.
Cochrane, D, et al., Model for the cost analysis of shunted hydrocephalic children. Pediatric Neurosurgery, 1995, vol. 23, pp. 14-19.
Seshadri, S., et al., Lifetime risk of dementia and Alzheimer's Disease. American Academy of Neurology, 1997, vol. 49, pp. 1498-1504.
Alzheimer's Association. Alzheimer's Disease Facts and Figures. Chicago : Alzheimer's Association, 2010.
Rekate, Harold L., Hydrocephalus in Adults. Apr. 2007, Neurosurgical Focus, vol. 22, p. (Introduction).
Burnett, Mark G., Sonnad, Seema S. and Stein, Sherman C., Screening tests for normal-pressure hydrocephalus: sensitivity, specificity, and cost. Journal of Neurosurgery, Dec. 2006, vol. 105, pp. 823-829.
Drake, James, et al., Randomized Trial of Cerebrospinal Fluid Shunt Valve Design in Pediatric Hydrocephalus. Neurosurgery, Aug. 1998, vol. 43, pp. 294-303.
Marmarou, Anthony, et al., Diagnosis and management of idiopathic normal-pressure hydrocephalus: a prospective study in 151 patients. Journal of Neurosurgery, Jun. 2005, vol. 102, pp. 987-997.
Williams, Michael A., et al., Influence of shunt surgery on healthcare expenditures of elderly fee-for-service Medicare beneficiaries with hydrocephalus. Journal of Neurosurgery, Jul. 2007, vol. 107, pp. 21-28.
Patwardhan, Ravish V. and Nanda, Anil, Implanted Ventricular Shunts in the United States: The Billion-Dollar-A-Year Cost of Hydrocephalus Treatment. Neurosurgery, Jan. 2005, vol. 56, pp. 139-145.
Simon, Tamara D., et al., Hospital care for children with hydrocephalus in the Unites States: utilization, charges, comorbidities, and deaths. Journal of Neurosurgery: Pediatrics, Feb. 2008, vol. 1, pp. 131-137.
Codman & Shurtleff, Inc. Life NPH. [Online] [Cited: Jul. 29, 2010] http://www.lifenph.com/faqs.asp.
National Institutes of Health. Hydrocephalus Fact Sheet. National Institute of Neurological Disorders and Stroke. [Online] Jul. 10, 2010. [Cited: Aug. 2, 2010] http://www.ninds.nih.gov/disorders/hydrocephalus/detail_hydrocephalus.htm.
Persson, Eva-Karin, et al., Hydrocephalus in children born in 1999-2002: epidemiology, outcome and ophthalmological findings. Childs Nervous System, 2007, vol. 23, pp. 1111-1118.

(56) References Cited

OTHER PUBLICATIONS

Browd, Samuel R., et al., Failure of Cerebrospinal Fluid Shunts: Part I: Obstruction and Mechanical Failure. 36, Pediatric Neurology, 2006, pp. 83-92.
Sgouros, Spyros. Spina Bifida Family Support. [Online] [Cited: Aug. 13, 2010] http://www.spinabifidasupport.com/defhydrocephalus.htm.
Examination Report mailed Nov. 13, 2015 in corresponding Australian Patent Application No. 2011227017, 6 pages.
Examination Report mailed Nov. 23, 2015 in corresponding European Patent Application No. 11710987.6, 4 pages.
Office Action mailed Oct. 21, 2015 in corresponding Chinese Patent Application No. 201180022356.X, 37 pages.
First Chinese Office Action dated Mar. 14, 2014 for CN 201180022356.X.
International Search Report and Written Opinion dated May 18, 2011 for PCT/US2011/029261 filed Mar. 21, 2011.
Restriction Requirement dated Jan. 28, 2015 for U.S. Appl. No. 13/636,115, filed Sep. 19, 2012.
Second Chinese Office Action dated Feb. 3, 2015 for CN 201180022356.X.
European Search Report mailed Jun. 26, 2015 in European App. No. 11710987.6, 4 pages.
European Search Report mailed Jun. 5, 2014 in European App. No. 11710987.6, 4 pages.
European Search Report mailed Otober 31, 2013 in European App. No. 11710987.6, 3 pages.
Akbar et al., Adjustable cerebrospinal fluid shunt valves in 3.0-Tesla MRI: A phantom study using explanted devices, Jul. 2010.
Inoue et al., Effect of 3-tesla magnetic resonance imaging on various pressure programmable shunt valves, Aug. 2005.
Lollis et al., Programmable CSF shunt valves: radiographic identification and interpretation, Aug. 2010.
Zhong et al., Advances in ICP monitoring techniques, Jun. 2003.
Final Office Action mailed Jun. 18, 2014 in corresponding U.S. Appl. No. 13/488,326, 18 pages.
Final Office Action mailed May 22, 2015 in corresponding U.S. Appl. No. 13/488,326, 10 pages.
Non-Final Office Action mailed Jan. 13, 2016 in U.S. Appl. No. 14/667,441, 28 pages.
Non-Final Office Action mailed Oct. 21, 2014 in corresponding U.S. Appl. No. 13/488,326, 27 pages.
Non-Final Office Action mailed Oct. 24, 2013 in corresponding U.S. Appl. No. 13/488,326, 25 pages.
Non-Final Office Action mailed Apr. 5, 2016 in U.S. Appl. No. 14/488,326, 22 pages.
Office Action mailed May 10, 2016 in Chinese patent application No. 201180022356.X, 13 pages.
European Search Report mailed May 4, 2016 in European App. No. 11710987.6, 5 pages.
Office Action mailed May 10, 2016 in Chinese patent application No. 201180022356.X, 32 pages.
Final Office Action mailed Oct. 20, 2016 in U.S. Appl. No. 13/488,326, 13 pages.
Exam Report mailed Sep. 15, 2016 in European Application No. 11710987.6, 3 pages.
Final Office Action mailed Aug. 30, 2016 in U.S. Appl. No. 14/667,441, 21 pages.
Office Action mailed Aug. 23, 2016 in China Application No. 201180022356.X.
European Examination Report mailed Feb. 14, 2017 in European Patent Application No. 11710987.6, 4 pages.
Examination Report mailed Feb. 7, 2017 in Canadian Patent Application No. 2793675, 3 pages.
Non-Final Office Action mailed Feb. 24, 2017 in corresponding U.S. Appl. No. 14/667,441, 24 pages.
Non-Final Office Action mailed Mar. 9, 2017 in U.S. Appl. No. 13/488,326, 13 pages.

\* cited by examiner

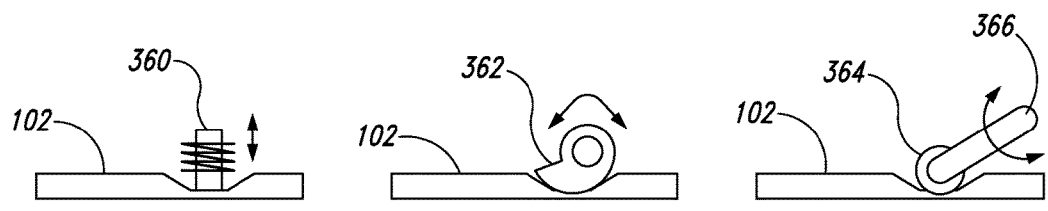
Fig. 3A  Fig. 3B  Fig. 3C
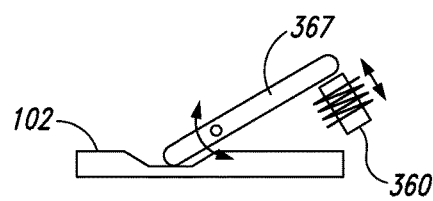 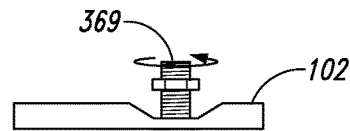
Fig. 3D  Fig. 3E
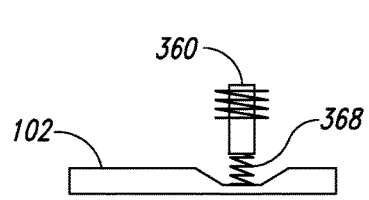 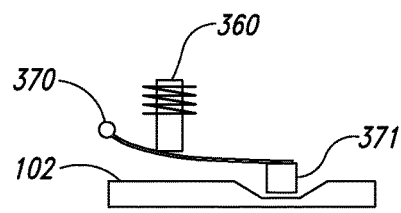
Fig. 3F  Fig. 3G

BODY FLUID DRAINAGE SYSTEM

CROSS-REFERENCE TO RELATED APPLICATION(S)

This application claims the benefit of U.S. Provisional Patent Application No. 61/315,660, entitled "FAILURE RESISTANT SHUNT," filed Mar. 19, 2010, and U.S. Provisional Patent Application No. 61/407,359, filed Oct. 27, 2010, entitled "EXTERNAL CSF DRAINAGE SYSTEM WITH IMPROVED VALVE AND OTHER FEATURES," both of which are incorporated herein by reference in their entireties.

TECHNICAL FIELD

The present technology relates generally to draining excess body fluids. In particular, several embodiments are directed toward body fluid drainage systems with enhanced drainage regulation and associated methods.

BACKGROUND

A variety of medical conditions cause the collection of excess body fluids within the human body. Hydrocephalus, for example, is an accumulation of excess cerebrospinal fluid ("CSF") in the ventricles of the brain that increases intracranial pressure ("ICP"). This condition can be caused by the inability to reabsorb CSF, impaired CSF flow, or excessive production of CSF. Acute accumulations of excess CSF can also occur from brain trauma, brain hemorrhaging, strokes, brain tumors, spinal fluid leaks, meningitis, and brain abscesses. When left untreated, hydrocephalus and other excess accumulations of CSF can progressively enlarge the ventricles of the brain, which can increase ICP and cause convulsions, mental disabilities, and eventually death.

Treatment for hydrocephalus generally requires the installation of a CSF shunt that drains CSF from the brain to an alternate location that can collect the excess CSF or reabsorb it into the body. A ventriculoperitoneal shunt ("VPS"), for example, includes a subcutaneously installed catheter inserted in the lateral ventricle (i.e., a site of excess CSF) and in fluid communication with the peritoneal cavity to facilitate reabsorbtion of the excess CSF into the body. A mechanical valve, generally implanted flush with the skull, can regulate CSF flow through the catheter. Recent innovations have resulted in VPSs that can regulate CSF movement based on static pressure parameters. For example, an external magnetic field can be applied to the implanted VPS to change the set point pressure of the valve.

Similar to hydrocephalus, acute accumulations of CSF are treated by shunting excess CSF to an alternate location. For example, temporary CSF diversion generally includes the installation of an external ventricular drain ("EVD") that funnels CSF from the lateral ventricle to an external drainage chamber, and thereby reduces the intracranial CSF volume and lowers ICP. Alternatively, temporary CSF diversion can include placing a lumbar drain ("LD") at the base of the spine, and draining CSF from the lumbar region to an external drainage chamber. Despite having different insertion points, EVDs and LDs use the similar components to control drainage.

In general, temporary and more permanent CSF diversion devices (e.g., VPSs) include similar features, and thus incur many of the same complications. Infection, for example, can be a significant risk factor both during and after implantation of a CSF shunt. When an infection occurs, the entire CSF shunt must be removed, and the patient must generally undergo 10-14 days of IV antibiotics and re-internalization of a new CSF shunt. Mechanical failure can occur within each component of a CSF shunt, and generally requires the replacement of the failed component(s). The inlet of the catheter, for example, can incur in-growth of intraventricular tissue. Valves can fail due to debris build-up (e.g., blood, protein) within the valve, and the outlet of the catheter can fail by fracturing, becoming obstructed, or tethering within scar tissue. These mechanical failures, infections, and other complications cause a majority of implanted CSF shunts to fail within two years and nearly all shunts fail within ten years. Due to this unreliability and the necessity to locally monitor and adjust ICPs, conventional CSF shunts require frequent intervention by medical professionals.

BRIEF DESCRIPTION OF THE DRAWINGS

FIGS. 3A-3J are side views of actuators for a valve device in accordance with embodiments of the present technology.

DETAILED DESCRIPTION

The present technology is directed to devices, systems, and methods for draining excess body fluids. In one embodiment, for example, a body fluid drainage system can be installed between a site of excess body fluid in a patient and a second location (e.g., an external receptacle, an internal cavity) that can collect and/or reabsorb the excess body fluid. The body fluid drainage system can include a valve device that applies incremental forces to an exterior of a catheter to regulate the drainage rate of the body fluid. In selected embodiments, the body fluid drainage system can also generate forced flow of the body fluid through the catheter to both prevent obstructions and perform diagnostics on the system. Certain specific details are set forth in the following description and in FIGS. 1A-8B to provide a thorough understanding of various embodiments of the technology. For example, several embodiments of body fluid drainage systems that shunt cerebrospinal fluid ("CSF") are described in detail below. The present technology, however, may be used to drain a variety of excess body fluids, such as peritoneal fluid, blood, water, and/or other body fluids. Additionally, the term "catheter" is used broadly throughout the application to refer to any suitable tubing or structure that includes a lumen through which body fluids can flow. Other details describing well-known structures and systems often associated with CSF and other body fluid drainage systems, shunts, biomedical diagnostics, etc. have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1A-8B.

As used herein, the term "force" refers to the interaction between an actuator and a catheter. This term is used broadly, and in some embodiments "pressure" is an equally valid term. Additionally, in selected embodiments, the actuator can apply a force or a pressure to the catheter by changing the position of the actuator mechanism (e.g., a linear shaft, a rotary shaft, a screw shaft) relative to the catheter, thus "actuator position" may also be used to describe the interaction between the actuator and the catheter.

Figure 1A:
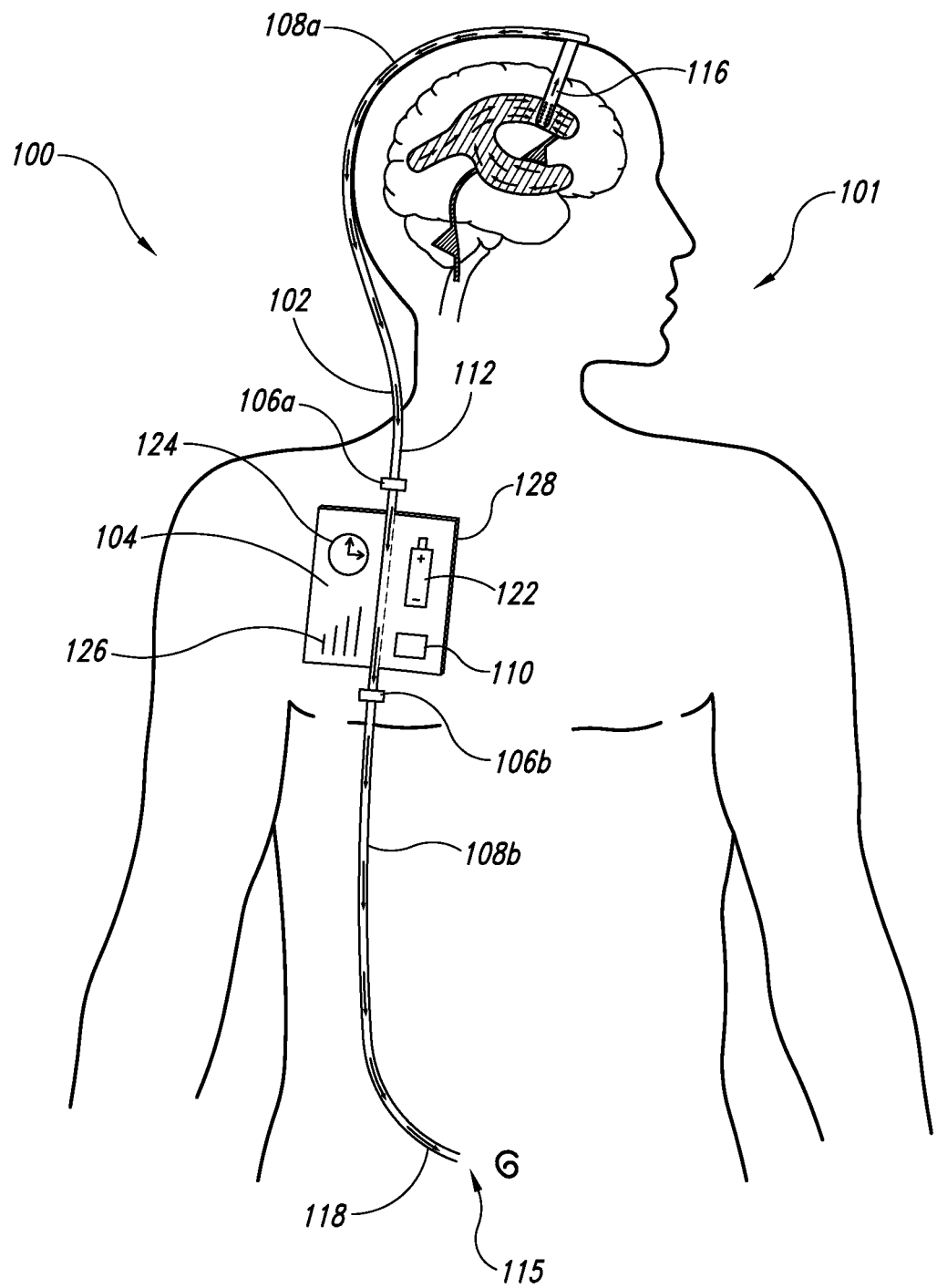
FIG. 1A is a schematic view of an internal body fluid drainage system installed within a patient in accordance with an embodiment of the present technology.

FIG. 1A is a schematic view of an internal body fluid drainage system 100 ("drainage system 100") implanted in a patient 101 in accordance with an embodiment of the present technology. The drainage system 100 can include a catheter 102, a valve device 104 over an exterior surface 112 of the catheter 102, and one or more sensors 106 (identified individually as a first sensor 106a and a second sensor 106b). The drainage system 100 can also include a controller 110 that is operatively coupled to the valve device 104 and/or the sensors 106. As described in further detail below, the valve device 104 can apply incremental forces to the exterior surface 112 of the catheter 102 to regulate body fluid flow through the catheter 102, and the controller 110 can alter the level of force applied by the valve device 104 on the catheter 102 in response to measurements (e.g., pressure, flow rate) taken from the sensors 106.

As shown in FIG. 1A, the catheter 102 can include a proximal portion 108a and a distal portion 108b opposite the proximal portion 108a. The proximal and distal portions 108a-b of the catheter 102 can be an integrally formed tube or include two or more separate tubes joined together using suitable fastening methods (e.g., gluing) known in the art. The catheter 102 can be made from a range of polymers, such as silicone, latex, thermoplastic elastomers, and/or other suitable tubing materials. In selected embodiments, portions of the catheter proximate to the valve device 104 can include compressible peristaltic pump tubing (e.g., silicone rubber, polyvinyl chloride), reduced fouling surfaces, tubing with different mechanical compliances, and/or other durable elastomeric materials that resist fatigue. In other embodiments, the catheter 102 can be made from tubing with biocides and/or other anti-biofouling agents that prevent organisms from entering the drainage system 100 and causing infection. When the catheter 102 includes different materials and/or sections of tubing, the different materials and/or portions can be sealed together with adhesives and/or other fasteners that provide a liquid-tight seal.

The proximal portion 108a of the catheter 102 is positioned at a site of excess body fluid and the distal portion 108b can be placed in fluid communication with an internal receptacle that collects and/or absorbs the body fluid. The proximal portion 108a of the catheter 102 can include an inlet region 116 with one or more openings (not visible) in fluid communication with a site of excess body fluid such that the body fluid can flow into the catheter 102. In the embodiment illustrated in FIG. 1A, for example, the inlet region 116 of the catheter 102 is installed (e.g., via a burr hole) into a ventricle 113 of the patient's brain to receive excess CSF. After entering the drainage system 100, the body fluid can travel in an antegrade flow through the catheter 102 to the distal portion 108b. The distal portion 108b can include an outlet region 118 that expels the excess body fluid into an internal location. For example, the outlet region 118 can be placed in fluid communication with the patient's peritoneal cavity 115, where excess body fluid can reabsorb into the body. In other embodiments, the outlet region 118 can expel the body fluid into the atrium of the heart, the pleural lining of the lung, the gallbladder, and/or other suitable terminal locations.

The valve device 104 can be positioned between the proximal and distal portions 108a-b of the catheter 102 to regulate the body fluid flow through the drainage system 100. As shown in FIG. 1A, for example, the valve device 104 can be implanted in a subclavicular pocket of the patient 101. In other embodiments, the valve device 104 can be installed in a prefascial or subfascial intra-abdominal region. This intra-abdominal positioning is particularly suited for neonates to ease exchange of the valve device 104 as the child grows, but also facilitates accessibility to the valve device 104 for adults. Advantageously, placement of the valve device 104 in either the subclavicular pocket or the intra-abdominal region negates the need to shave the patient's scalp to perform cranial surgery in the event that a component requires replacement or repair, and thus avoids the need for repeated incisions in the scalp that can cause devascularization, poor wound healing, and/or infection. The intra-abdominal valve device 104 also eases the periodic replacement of batteries or other power sources. In other embodiments, the valve device 104 can be installed subcutaneously in other regions of the torso or between another site of excess body fluid and a receptacle that can collect and/or reabsorb the body fluid. In further embodiments, the valve device 104 can be miniaturized such that it can be implanted under the scalp.

The sensors 106 can measure pressure within the catheter 102, flow rate of the body fluid through the catheter 102, and/or other desired measurements associated with body fluid drainage through the drainage system 100. Pressure sensors can be small electrical sensors positioned along the drainage device 100. Body fluid flow rate through the catheter 102 can be measured with a non-electrical Rotameter that uses a local or remote sensor to read the position of a weighted or buoyant ball that rises and falls within the catheter 102 in proportion to the flow rate. In other embodiments, the body fluid flow rate can be measured using what is known in the art as the "ice cube test." An improved version of such a flow rate sensor includes a resistive electrical heater and temperature sensor embedded in the body fluid flow, rather than an external heater/cooler and an external temperature measurement device used in conventional ice cube tests. In further embodiments, body fluid flow rate can be measured using what is known as a "tick-tock chamber" that senses the rate that specialized chambers refill with the body fluid within the catheter 102.

As shown in FIG. 1A, the sensors 106 can be positioned proximate to the outlet and inlet to the valve device 104. Accordingly, the first sensor 106a can measure the flow rate and/or the pressure within the proximal catheter 108a before it enters the valve device 104 and the second sensor 106b can measure the flow rate and/or pressure within the distal portion 108b as it exits the valve device 104. This information can be used to ensure the valve device 104 generates the desired drainage rate, to monitor patient orientation, to perform diagnostics on the drainage system, and/or derive other desired measurements or characteristics. In other embodiments, the drainage system 100 can include more or less sensors 106. For example, a pressure sensor 106 can be positioned proximate to the inlet region 116 to measure ICP directly.

The sensors 106 can also be used to derive a pressure at a desired location (e.g., the Foramen of Monroe for ICP) spaced apart from the sensors 106. For example, the sensors 106 that are positioned proximate to the valve device 104 in the torso of the patient 101 can be used to derive ICP. As shown in FIG. 1A, the sensors 106 can be positioned on either side of the valve device 104 to measure pressure upstream and downstream of the valve device 104. When the patient 101 is upright (i.e., standing), the first sensor 106a at the proximal portion 108a can measure a pressure that is substantially equal to the ICP plus the pressure head created by the body fluid in the proximal portion 108a above the first sensor 106a. The second sensor 106b at the distal portion 108b can measure a pressure substantially equal to the pressure at the outlet region 118 (e.g., the peritoneal cavity 115; as is known in the art, the pressure is approximated as zero relative to atmosphere) plus the negative pressure created by the body fluid in the distal portion 108b below the second sensor 106b. The pressures from the upstream and downstream sensors 106 can be combined to derive the true ICP. For example, when the valve device 104 is positioned midway between the ventricle 113 and the outlet region 118, the summation of the two pressure measurements from the sensors 106 negates the contribution of pressure head and provides the true ICP.

In other embodiments, as described in greater detail below with reference to FIGS. 7A-7D, a pressure reference line can be coupled to the drainage system 100 and used to compensate for changes in patient position. The pressure reference line measures the pressure head between a desired reference location and the sensor 106 at the valve device 104 directly. As such, the desired pressure measurement (e.g., ICP) is simply the difference between the two measured pressures as taken from two independent sensors (i.e., the pressure reference line sensor and the drainage line sensor) or a single differential pressure sensor.

The drainage system 100 can also include an orientation sensor (not shown) to accurately measure a desired pressure (e.g., ICP) regardless of the orientation of the patient 101. For example, the orientation sensor can include an accelerometer, inclinometer, and/or other orientation sensing device. The orientation sensor is used to determine the angle of repose (i.e., standing, lying, or therebetween); such that the measured angle and the known length of the proximal portion 108a of the catheter 102 can be used to calculate the pressure head. The pressure head can be subtracted from the measured pressure to calculate the true ICP.

The controller 110, e.g., a microprocessor, can read the measurements taken from the sensors 106 (e.g., pressure, flow rate, orientation, etc.), store such measurements and other information in a database, adjust the position of the valve device 104, and/or carry out algorithms to regulate fluid flow through the drainage device 100. For example, the controller 110 can compare pressure measurements from the sensors 106 with a desired ICP to determine whether to incrementally open or close the valve device 104 and by what percentage. For example, when the pressure is lower than a desired pressure, the controller 110 can incrementally close the valve device 104 to increase the resistance to antegrade flow through the catheter 102. If the sensed pressure is higher than desired, the controller 110 can incrementally open the valve device 104 to decrease the resistance to antegrade flow. Similarly, the controller can also compare the sensed flow rate with a desired flow rate, and adjust the position of the valve device 104 accordingly. The controller 110 can also carry out an algorithm that moves the valve device 104 a predetermined amount each time a measurement outside of a desired limit (e.g., desired CSF range) is detected. Such a control algorithm can also relate the incremental movement of the valve device 104 to the magnitude of the difference between a desired and a measured value. In other embodiments, a proportional-integral-derivative ("PID") control algorithm or variations thereof (e.g., P-only, PI-only) can control the movement of the valve device 104. As such, the controller 110 can manage body fluid flow in real-time to maintain the ICP and/or other desired parameter within appropriate limits across a range of changes in pressure or body fluid generation rate caused by physiologic processes (e.g., valsalva maneuvers, changes in body orientation).

The controller 110 can include algorithms that save power. For example, a tolerance window on the control parameter (e.g., ICP or CSF flow rate) can be defined such that the valve device 104 does not change position within the tolerance window. As another example, the time between sensor measurements can be adjusted based on the error between the desired set point and the measured value, such that less frequent measurements are made during periods of small error. These power-saving control algorithms can also be adapted to the dynamics of the specific application. During CSF drainage, for example, significant changes in CSF production may occur over several hours such that only infrequent sensor measurements and valve device 104 movements are necessary for adequate flow control. As such, the controller 110 can be configured to ignore unimportant transient conditions (e.g., ICP oscillations due to the cardiac cycle, ICP increases due to coughing or movement) removed by averaging sensor measurements and/or frequency filtering.

Additionally, the controller 110 can also include logic to clear the valve device 104 of obstructions by incrementally opening the valve device 104 until the obstruction clears. For example, the controller 110 can be configured to maintain a desired ICP such that when an obstruction within the valve device 104 causes an increase in the measured pressure, the control algorithm (e.g., a proportional-integral-derivative) incrementally or fully opens the valve device 104 to decrease the resistance to antegrade flow. This incremental opening of the valve device 104 allows the obstruction to flow through the valve device 104 such that the drainage system 100 can maintain the desired ICP. As described in further detail below, in other embodiments, the controller 110 can include logic that clears and/or prevents obstructions by flushing the catheter 102 with body fluid.

As further shown in FIG. 1A, the drainage system 100 can include a time keeping device 124 (e.g., clock, timer, etc.) that is operatively coupled to the controller 110. The controller 110 can use the time keeping device 124 to sense pressure and/or flow rate at preset time intervals (e.g., once a minute). Additionally, as explained in further detail below, the controller 110 can use the time keeping device 124 to periodically flush the catheter 102 and/or periodically run diagnostics.

Additionally, as shown in FIG. 1A, the drainage system 100 can also include a power source 122 for the valve device 104 and/or other electrical features (e.g., the time keeping device 122, the sensors 106, etc.). The power source 122 can be stored locally within the drainage system 100. As such, the power source 122 can thus include a lithium-ion cell, a rechargeable battery, and/or other suitable portable power sources. In selected embodiments, the internally installed power source 122 can be recharged remotely using inductive coupling, kinetic energy generation by M2E of Boise, Id., and/or other remote recharging methods known in the art. In other embodiments, the drainage system 100 can connect to an external recharging station.

In selected embodiments, the controller 110 can be operatively coupled to a wireless communication link 126, such as a WiFi connection, radio signal, and/or other suitable communication links that can send and/or receive information. The wireless communication link 126 allows measurements from the sensors 106 and/or other information to be monitored and/or analyzed remotely. For example, the wireless communication link 126 allows measurements recorded from the sensors 106 to be accessed at a doctor's office, at home by the patient 101, and/or at other remote locations. Additionally, the drainage system 100 can use the wireless communication link 126 to receive information at a WiFi hot spot or other remotely accessible locations. This allows a remote physician to inquiry the drainage system 100 regarding particular measurements (e.g., ICP), instruct the controller 110 to adjust the valve device 104 accordingly, and/or program sophisticated algorithms onto the controller 110 for the drainage system 100 to carry out. Accordingly, the drainage system 100 can provide more expedient, sophisticated, and personalized treatment than conventional CSF shunts, without requiring frequent in-office visits.

As further shown in FIG. 1A, the valve device 104, the controller 110, and/or other subcutaneously implanted features of the drainage system 100 can be enclosed within a housing 128. Accordingly, the housing 128 can be made from a biocompatible material that protects the devices stored within from tissue ingrowth, body fluids, and/or other internal bodily features that may interfere with the operability of the drainage system 100. In selected embodiments, the housing 128 can also form a magnetic shield over the devices within it such that the patient 101 can undergo magnetic resonance imaging ("MRI") and similar procedures without removing the drainage system 100.

In operation, the drainage system 100 can have generally low power consumption. For example, the drainage system 100 requires minimal, if any, continuous power. In one embodiment, the time keeping device 124 is the only feature of the drainage system 100 that continuously draws from the power source 122. Other devices can draw from the power source 122 intermittently as needed. For example, the sensors 106 and/or other sensing devices can sense pressure at preset intervals (e.g., once per minute) and only draw from the power source 122 at that time. Similarly, any diagnostics and/or forced flows (e.g., backflushing, described below) only occur periodically and thus only require power occasionally. In selected embodiments, the valve device 104 only requires power when it changes position to adjust the pressure and/or flow rates. Without the need for any continuous substantial power, the drainage system 100 consumes much less power than would be required using a pump to drive body fluid. As described below, the drainage system 100 can also include a hybrid mechanical and electrical device that reduces the required frequency of actuator movements, and thus further reduces power consumption. Accordingly, the drainage system 100 can be configured such that the power source 122 runs the drainage system 100 for extended periods of time (e.g., five or more years), and therefore does not necessitate frequent surgeries to replace the power source 122.

Optionally, the drainage system 100 can also include a pump (e.g., an electro-osmotic pump) that can be activated to drive body fluid flow through the drainage system 100. For example, the controller 110 can include logic that activates the pump when the orientation of the patient 101 is such that the body fluid flows in the reverse direction (i.e., retrograde flow) through the catheter 102. In other embodiments, the drainage system 100 can include other suitable devices and features that facilitate the controlled drainage of body fluids.

The subcutaneously installed drainage system 100 shown in FIG. 1A can also include features that limit the risk of infection during and after implantation. For example, components of the drainage system 100 (e.g., the catheter 102, the housing 128) can include anti-fouling coatings and/or antibiotic impregnated materials. In selected embodiments, short-term thermal cooling and heating can be applied to the drainage system 100 as a whole or components thereof to reduce bacterial colonization during the perioperative period. In other embodiments, the housing 128, the valve device 104, and/or other portions of the drainage system 100 can be magnetized or otherwise treated to reduce bacterial growth and contamination.

Figure 1B:
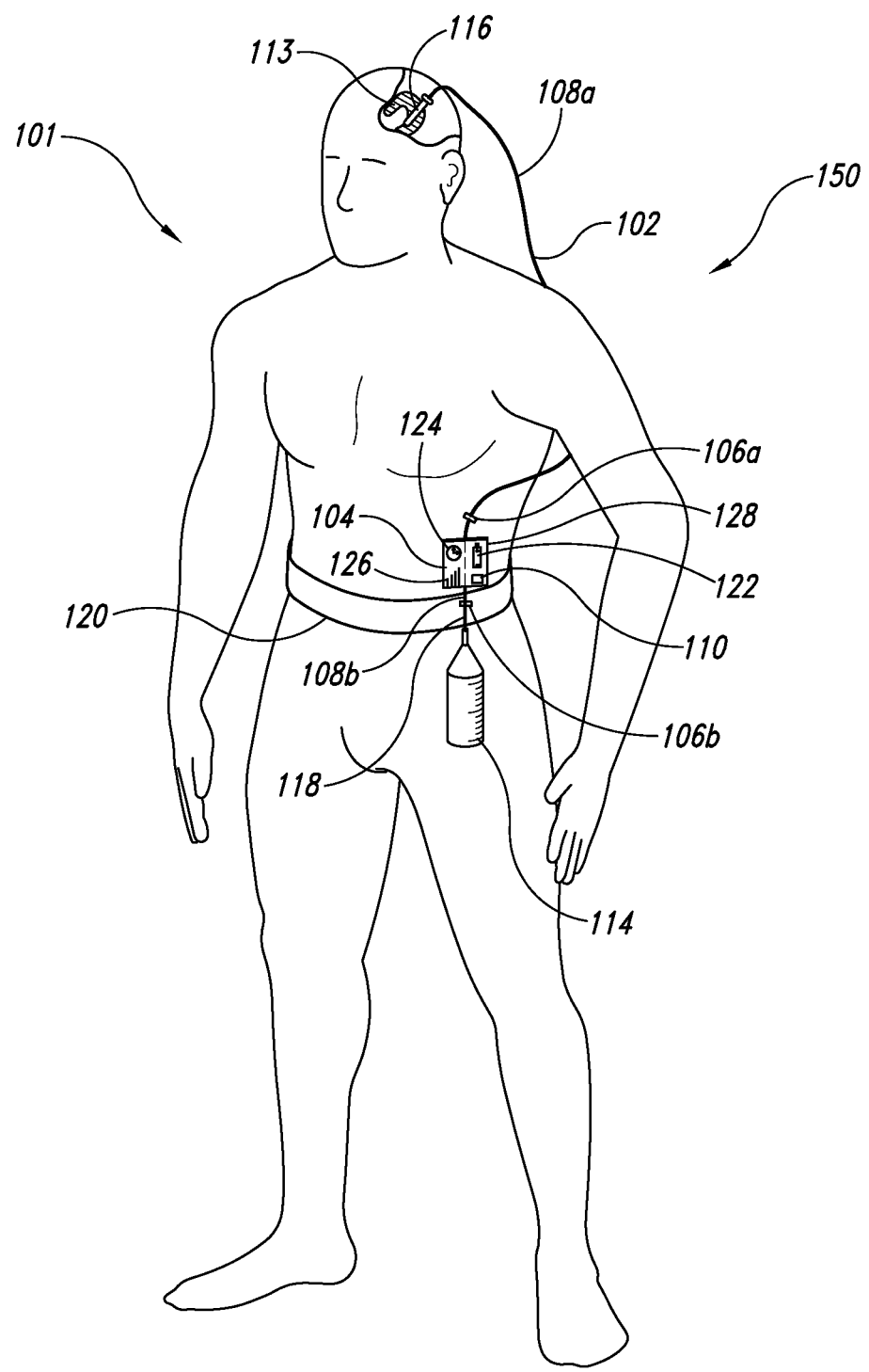
FIG. 1B is a schematic view of an external body fluid drainage system installed in a patient in accordance with an embodiment of the present technology.

FIG. 1B is a schematic view of an external body fluid drainage system 150 ("drainage system 150") implanted in the patient 101 in accordance with an embodiment of the present technology. The drainage system 150 includes features generally similar to the drainage system 100 described above with reference to FIG. 1A. For example, the drainage system 150 can include the catheter 102 having the proximal portion 108a and the distal portion 108b, the valve device 104 positioned therebetween, the sensors 106, and the controller 110 operatively coupled to the sensors 106 and the valve device 104. Additionally, like the internal drainage system 100 described above, the external drainage system 150 can regulate CSF or other excess body fluid flow using sophisticated and individualized methods, and do so while operating as a low power system. However, the drainage system 150 shown in FIG. 1B is installed externally, between the ventricle 113 and an external receptacle 114. The external receptacle 114 can be placed in fluid communication with the outlet region 118 of the catheter 102 such that it can collect the excess body fluid. As such, the external receptacle 114 can be a bag or container made from a range of polymers (e.g., silicone, polyvinyl chloride) and/or other suitable materials for storing body fluids.

In the illustrated embodiment, the external receptacle 114 is secured to the midsection of the patient 101 with a belt 120 such that the patient 101 can remain mobile as the drainage system 150 removes the excess body fluid. As shown in FIG. 1B, the belt 120 can also carry the housing 128 that contains the valve device 104, the controller 110, and/or other devices that operate the drainage system 150. The externally positioned housing 128 can be made from a durable material (e.g., plastic) that can withstand the rigors of the outside environment and substantially protect the components within. Snaps, thread, hooks, and/or other suitable fasteners can be used to secure the external receptacle 114 and/or the housing 128 to the belt 120. In other embodiments, the external receptacle 114 and/or the housing 128 can be secured to other portions of the patient 101 that do not substantially inhibit the patient's mobility.

In further embodiments, such as when the drainage system 100 is used for temporary shunting of acute accumulation of the body fluid, the external receptacle 114 can be hung on a pole commonly used for IV bags or otherwise affixed to an external structure. Additionally, for temporary drainage, the devices within the housing 128 can also be positioned apart from the patient 101, such as on a console connected with a power source.

Figure 2A:
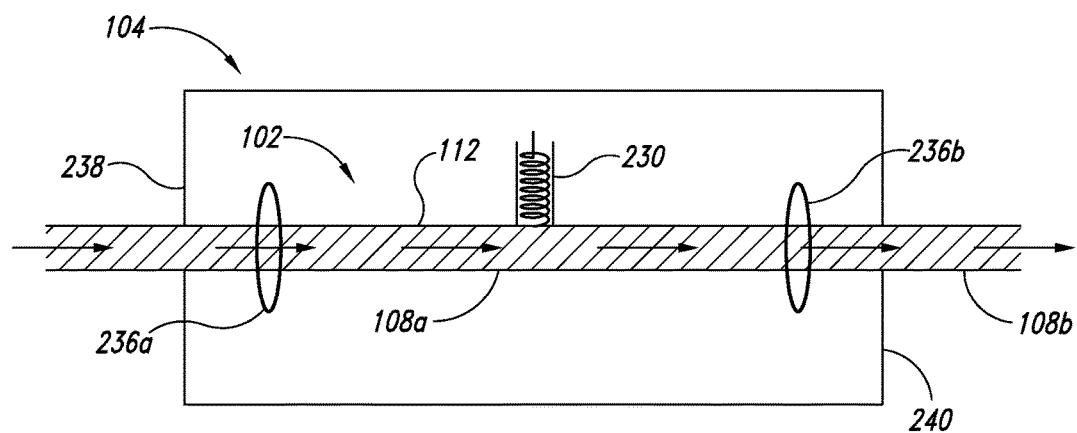
FIG. 2A is an enlarged schematic, cross-sectional view of a valve device in accordance with an embodiment of the present technology.

FIG. 2A is a schematic cross-sectional view of the valve device 104 for use with the body fluid drainage systems 100 and 150 shown in FIGS. 1A and 1B and configured in accordance with an embodiment of the present technology. As shown in FIG. 2A, the valve device 104 can include an actuator 230 positioned over a portion of the catheter 102. The actuator 230 can apply varying forces to the external surface 112 of the catheter 102 to regulate the body fluid flow rate therein. The surface with which the actuator 230 contacts the catheter 102 can vary in size and shape. For example, the contact surface can be flat, rounded, and/or have a different profile or shape. The contact surface can also vary in length along the axis of the catheter 102 to spread the force of the actuator 230 across the catheter 102. For example, controlling drainage of CSF can be accomplished using contact lengths of a few millimeters to a few centimeters.

In the illustrated embodiment, the actuator 230 contacts one side of the catheter 102 to compress or "pinch" the catheter 102. In other embodiments, the actuator 230 can apply force from opposing sides of the catheter 102 or apply force from multiple angles around the circumference of the catheter 102 to effectuate a similar compression or pinching action. This external compression eliminates the mechanical valve parts within the catheter 102, and thus prevents the actuator 230 from coming into contact with the body fluid within the catheter 102. Accordingly, the body fluid has a clear flow path through the catheter 102 that substantially reduces or eliminates stagnant flow regions (e.g., internal mechanical parts) and obstructions (e.g., build-up on the internal mechanical parts) often caused by the complex flow pathways common to conventional shunts. Additionally, in selected embodiments, the actuator 230 can be configured to fail in the open position (i.e., not restricting flow) such that it does not to impede drainage of the body fluid.

The actuator 230 can incrementally or continuously change the flow resistance of the catheter 102 to regulate drainage rate of the body fluid. For example, rather than a binary open-closed valve, the actuator 230 can compress the catheter 102 varying degrees between the open and closed positions. The actuator 230 can thus adjust the level of compression to accommodate a multitude of variables, and precisely regulate flow rate through the catheter 102. For example, CSF drainage devices (e.g., the drainage devices 100 and 150 shown in FIGS. 1A and 1B) can vary the compression of the actuator 230 in response to the patient's orientation, a siphoning condition, ICP, retrograde flow, peritoneal pressure, and/or other variables that affect the desired flow rate. Thus, the valve device 104 provides sophisticated control of the body fluid drainage.

Advantageously, despite this precise control, the valve device 104 can also have generally low power requirements because the valve device 104 only requires power as it adjusts the position of actuators 230. Once at a desired position, the actuator 230 can maintain its position without power (e.g., "self-braking"). Piezo-electric actuators (e.g., the Squiggle Motor by Newscale Technologies of Victor, N.Y.) include such incremental movement and self-braking features. Advantageously, piezo-electric actuators 230 can also be small, consume little power when they do move, but can also provide significant force on the catheter 102. Piezo-electric actuators can also be compatible with MRIs. In selected embodiments, the valve device 104 can also be configured to permit fluctuation within a desired range (e.g., cardiac effects) and/or transient spikes or troughs (e.g., coughing) in pressure and/or flow rate. This prevents the actuator 230 from unnecessarily changing positions and unnecessarily consuming power. In other embodiments, the self-braking actuator 230 can be combined with a variable resistance component (e.g., a compliant interface member described in FIGS. 3F-3H) such that the valve device 104 can operate indefinitely without power as long as the pressure and/or flow rate remain within the desired limits. These reduced power features of the valve device 104 can be of particular advantage for internally implanted valve devices 104 (e.g., the drainage system 100 shown in FIG. 1A) because it increases the lifetime of the power source 122 between recharging cycles or surgeries to replace the power source 122.

The actuator 230 can also be configured to close to prevent any undesired retrograde flow through the catheter 102. For example, the sensors 236 can detect a pressure gradient directed toward the proximal portion 108a of the catheter 102 (e.g., toward the brain) that may be caused by patient orientation (e.g., upside-down), straining of the abdomen, low ICPs, and/or other conditions that may induce retrograde flow. In response to this negative pressure gradient, the controller 110 (FIGS. 1A and 1B) can close the actuator 230 to obstruct all flow through the valve device 104. In other embodiments, flow sensors and/or pressure sensors positioned elsewhere along the drainage systems 100 and 150 can sense retrograde flow and trigger the closing of the actuator 230. Alternatively, the valve device 104 can include a one-way check valve as a purely mechanical method to prevent retrograde flow such that monitoring for retrograde flow with the controller 110 is not required.

The force applied by each of the actuator 230 to the exterior surface 112 and/or the effect thereof can be monitored by sensors 236 (identified individually as a first pressure sensor 236a and a second pressure sensor 236b). As shown in FIG. 2A, the sensors 236 can be positioned proximate to an inlet portion 238 and an outlet portion 240 of the valve device 104 to measure the pressure and/or flow rate within the catheter 102 before and after the body fluid exits the valve device 104. The controller 110 can analyze these pressure or flow rate measurements to determine whether the valve device 104 produced a desired pressure or flow rate, and adjust the positions of the actuator 230 accordingly. In other embodiments, additional sensors 236 can be coupled to other portions of the catheter 102 to measure additional pressures, flow rates, and/or other desired properties of the flow through the valve device 104/

The actuator 230 and the sensors 236 can also be used to diagnose flow problems in the catheter 102. For example, the actuator 230 can be closed, and the pressure response can be measured over time and compared to an expected pressure for unobstructed flow, to the expected time required for the pressure to return to a baseline value, and/or to other pressure related values that can interpret fluid flow. Closing the actuator 230 during unobstructed flow results in a generally rapid increase in the pressure measurement upstream of the valve device 104, and opening the actuator 230 results in a rapid decrease in the pressure measurement as fluid freely flows through the distal portion 108b of the catheter 102. Little or no pressure increases observed upon closing the actuator 230 indicates an obstruction in the proximal portion 108a, while a slow decrease in pressure upon opening the actuator 230 indicates an obstruction in the distal portion 108b. These flow diagnostics can be performed routinely to sense obstructions at their onset. Additionally, the valve device 104 can be configured to perform these diagnostic tests more frequently when the potential for obstructions is higher (e.g., after surgery).

In other embodiments, diagnostics can be performed during normal operation (i.e., no specialized movement and no forced flow) of the drainage systems 100 and 150. For example, when the valve device 104 uses pressure-based control to maintain a constant pressure (e.g., ICP), an actuator 230 consistently operating at a fully-open position can indicate a blocked valve device 104 or an obstructed distal portion of the catheter 102. Conversely, an actuator 230 consistently operating in a fully-closed position can indicate an obstructed proximal portion 108a of the catheter 102.

In other normal operation flow diagnostics, pressure levels within a patient can be tracked (e.g., remotely via the wireless communications link 126 shown in FIGS. 1A and 1B) and characterized as "acceptable" or "unacceptable" pressure levels. In the case of a CSF drainage system, for example, an unacceptable level may be one that induces a headache. Using this information, the controller 110 can adjust the valve device 104 to maintain acceptable ranges of pressure for the particular patient. Thus, the diagnostic control of the valve device 104 can provide precise and individualized treatment to ensure not only that the excess body fluid is adequately drained, but also adjust to the particularities of each patient's needs.

In other embodiments, flow rate measurements, rather than or in conjunction with pressure measurements, can also be used to perform diagnostic tests and diagnose blockages. Similar to the pressure sensor driven diagnostics, Rotameters, the "ice cube test," the tick-tock chamber, and/or other flow rate sensors can measure flow rate during forced or unforced flow and compare it with a desired flow rate to identify partial or complete blockages.

In other embodiments, the valve device 104 can include more than one actuator 230. For example, the valve device 104 can include multiple actuators 230 to provide redundancy in the event an actuator 230 fails. Additionally, the inlet and outlet portions 238 and 240 can include multiple actuators 230 in order to vary the location of constrictions. This allows the actuators 230 to constrict alternate portions of the catheter 102 when others have debris build up. In further embodiments, selected actuators 230 can be designated solely to close the catheter 102 to obstruct antegrade flow. Other actuators 230 can adjust continuously between the open and closed positions to regulate flow rate as described above.

Figure 2B:
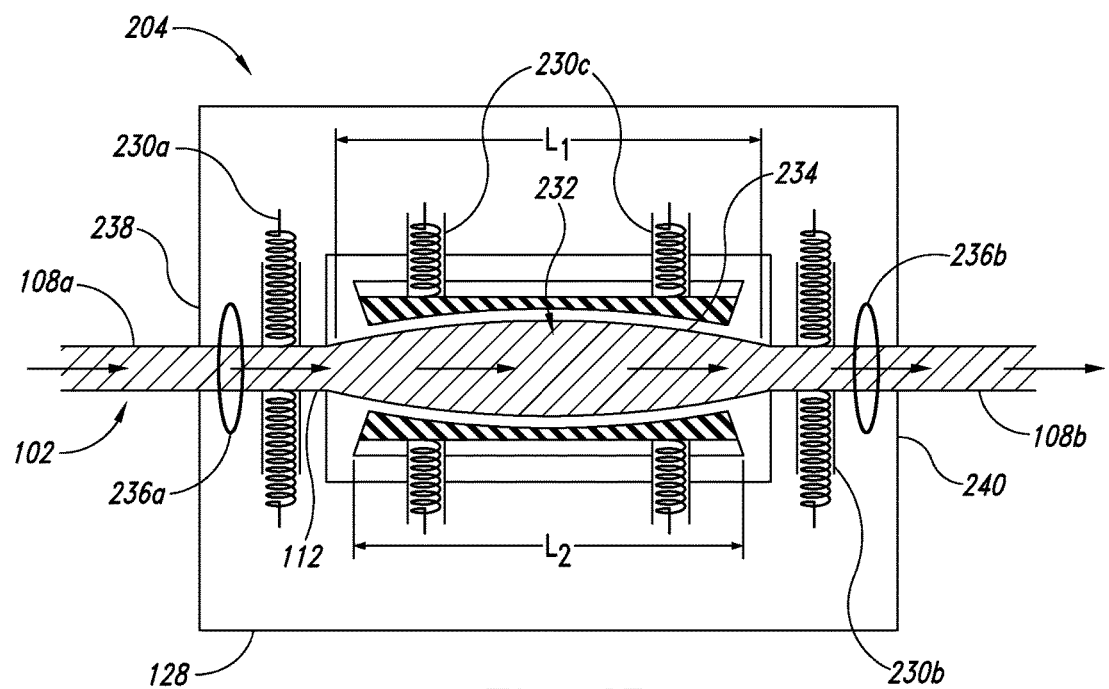
FIG. 2B is an enlarged schematic, cross-sectional view of a valve device in accordance with another embodiment of the present technology.

FIG. 2B is a schematic cross-sectional view of a valve device 204 in accordance with another embodiment of the disclosure. The valve device 204 includes features generally similar to the valve device 104 shown in FIG. 2A. For example, the valve device 204 includes the sensors 236 and the incrementally adjustable actuator 230 at the exterior surface 112 of the catheter 102. However, the valve device 204 shown in FIG. 2B includes additional actuators 230 (identified individually as a first actuator 230a, a second actuator 230b, and a third actuator 230c) positioned over different portions of the catheter 102. One or more of the actuators 230 can provide the incremental force at the exterior surface 112 of the catheter 102 in order to regulate flow and/or include power-saving self-braking features. Accordingly, like the valve device 104 shown in FIG. 2A, the valve device 204 can provide sophisticated flow control, but also benefit from the low power consumption described above. Additionally, the position of each actuator 230 can be adjusted independently by the controller 110 to produce the desired flow rate of the body fluid through the catheter 102.

In the embodiment illustrated in FIG. 2B, the valve device 204 further includes a reservoir 232 positioned between the proximal and distal portions 108a-b of the catheter 102. The reservoir 232 and the proximal and distal portions 108a-b can include generally similar materials and can be formed integrally or sealed together with adhesives and/or other fasteners that provide a liquid-tight seal. As shown in FIG. 2B, the reservoir 232 can have an exterior surface 234 and a larger cross-sectional dimension than a cross-sectional dimension of the catheter 102 such that the reservoir 232 retains a larger volume of the body fluid per cross-section than the catheter 102. In the illustrated embodiment, the proximal portion 108a, the reservoir 232, and the distal portion 108b can form a single lumen through which the body fluid can flow. This singular lumen provides a simple flow path for the body fluid that can reduce or eliminate obstruction-prone areas (e.g., corners, intersections between lumens) that exist in more intricate flow paths.

The reservoir 232 allows the valve device 204 to create forced flow or "flushing" through the proximal and distal portions 108a-b of the catheter 102 to clear obstructions within the catheter 102 and/or enable diagnostics of flow obstructions. For example, the valve device 204 can compress the reservoir 232, and the controller 110 or remote device can interpret pressure and/or flow rate changes of the forced flow to identify partial or complete blockages. The valve device 204 can also periodically evacuate the reservoir 232 toward the proximal and/or distal portions 108a-b of the catheter 102 to break up any build up within the catheter 102, and thereby reduce the likelihood of obstructions. The flow diagnostics and flushing can be performed routinely sense and remove obstructions at their onset. The valve device 204 can also perform diagnostic tests more frequently when the potential for obstructions is higher (e.g., after surgery).

In the illustrated embodiment, the third actuator 230c contacts a large portion of the exterior surface 234 of the reservoir 232 such that it more rapidly accelerates the volume of body fluid out of the reservoir 232. For example, as shown in FIG. 2B, the reservoir 232 has a first length $L_1$ and the third actuator contacts the exterior surface 234 of the reservoir 232 along a second length $L_2$ that is substantially equal to the first length $L_1$. This increased contact area provides a greater forced flow that can be used to remove obstructions (e.g., protein build up), run diagnostics, or otherwise flush the catheter 102 with the body fluid. In selected embodiments, the third actuator 232c can linearly apply force to the reservoir 232 along the second length $L_2$ to push the body fluid in a desired direction (e.g., toward the proximal portion 108a or the distal portion 108b). In other embodiments, the backflushing and/or forward flushing can be performed manually by the patient or caregiver by pressing on the reservoir 232 and directing the body fluid in the desired direction. The backflushing, forward flushing, and diagnostic operations can be performed either in an implantable drainage system 100 or an external drainage system 150.

The valve device 204 shown in FIG. 2B can also be used in conjunction with a conventional valve to add flushing and diagnostic operations (e.g., with flow regulation provided fully or partially by the conventional valve). For example, to retrofit the conventional drainage system, the valve device 204 can be placed in fluid communication with a conventional valve device (e.g., a mechanical ball in seat valve device). The valve device 204 can then adjust the actuators 230 to generate forced flow and/or incrementally regulate fluid flow. If only forced flow is desired, the valve device 204 need only include the reservoir 232 and one or more binary actuators that can accumulate body fluid in the reservoir 232 and expel it periodically as desired. As such, forced flow diagnostics can be performed periodically on the conventional drainage system to detect obstructions in the flow path of the body fluid. For example, the reservoir 232 can flush a portion of the conventional system, and the pressure response can be compared with the pressure and/or pressure decay of an unobstructed flow path. When used with a separate valve, the pressure response can be used to test the pressure-flow characteristics of the conventional valve to monitor its degradation over time. Alternatively, the flow rate can be monitored to detect obstructions and/or monitor the degradation of the conventional valve device.

Figure 3H:
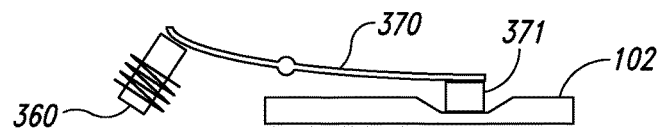

FIGS. 3A-3J are side views of actuators for a body fluid drainage system (e.g., the drainage systems 100 and 150 shown in FIGS. 1A and 1B) in accordance with embodiments of the present technology. Each of the actuators shown in FIGS. 3A-3J are pinch actuators that are incrementally and/or continuously adjustable between the open and closed positions. Therefore, as described above, the actuators can compress the catheter 102 and/or the reservoir 232 (FIG. 2B) to incrementally regulate body fluid flow. FIG. 3A, for example, shows a linear actuator 360 that can move in the directions indicated by the arrows to incrementally compress the catheter 102, and thereby change the resistance within the catheter 102. Any of the embodiments described below can be combined, can include interface members that transfer force from the actuator to the catheter 102, and/or can include other types of actuators, interface members, and/or compliant interface members that incrementally compress the catheter 102.

FIGS. 3B-3E illustrate embodiments of rotary actuation. For example, FIG. 3B illustrates a cam actuator 362 that compresses the catheter 102 by adjusting the amount of its rotation along the catheter 102. FIG. 3C shows a lever actuator 366 that transmits force to an interface member, such as a contact pad or a contact roller 364. As indicated by the arrows, the lever actuator 366 can rotate about a fulcrum to vary the degree at which the contact roller 364 compresses the catheter 102. In the embodiment shown in FIG. 3D, the linear actuator 360 of FIG. 3A rotates a lever 367 (i.e., the interface member contacting the catheter 102) about the catheter 102 to incrementally increase the resistance within the catheter 102. As shown in FIG. 3E, another rotary actuator, a screw actuator 369, can rotate in one direction to apply more force to the catheter 102 and rotate in the opposite direction to release force on the catheter 102.

FIGS. 3F-3H show actuators that include a compliant interface member between the linear actuator 360 shown in FIG. 3A and the catheter 102. In other embodiments, the actuators shown in FIGS. 3F-3H can use rotary or other types of actuation. Referring to FIG. 3F, the compliant member can include a spring 368 or other compliant material that transmits force from the actuator 360 to the catheter 102 to control flow. As shown in FIGS. 3G and 3H, the compliant member can also include a spring lever or other flexible lever 370 that rotates about a fulcrum 371 at the catheter 102. In the embodiment illustrated in FIG. 3G, the actuator 360 presses down on the flexible lever 370 to rotate it varying degrees and transmit the force from the actuator 360 to the catheter 102. In the embodiment illustrated in FIG. 3H, the actuator 360 can apply force upward against the flexible lever 370 such that it rotates and transfers force from the actuator 360 to the catheter 102. In operation, the spring 368, the flexible lever 370, and/or other compliant interface members provides a degree of passive actuation that adjust the force applied to the catheter 102 without moving the actuator 360. Accordingly, body fluid drainage systems (e.g., the drainage systems 100 and 150 shown in FIGS. 1A and 1B) including passive actuators can consume less power.

Figure 3I:
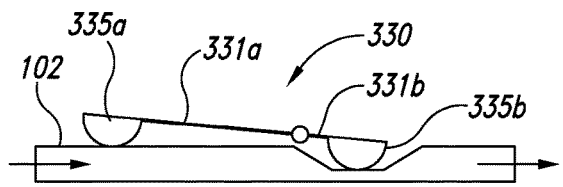
Figure 3J:
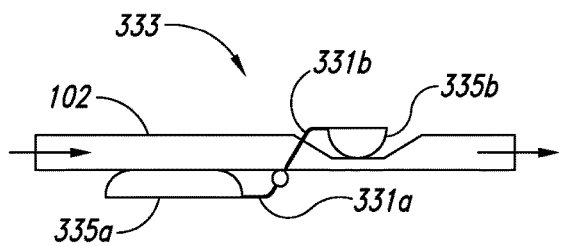

FIGS. 3I and 3J show purely mechanical actuators that require no power to operate. For example, FIG. 3I shows an actuator 330 that can regulate the flow rate through the catheter 102. The actuator 330 can include actuator contacts 335 (identified individually as a first actuator contact 335a and a second actuator contact 335b) connected to one another by a lever arm 331 having a first lever arm portion 331a and a second lever arm portion 331b. The desired flow rate characteristics of the actuator 330 can be obtained by changing the relative lengths of the first and second lever arm portions 331a-b and the relative areas of the first and second actuator contacts 335a-b. As shown in FIG. 3I, when the upstream pressure increases, the force on the first actuator contact 335a increases. The lever arm 331 transmits this force to the second actuator contact 335b such that it compresses the catheter 102. The force on the catheter 102 increases the valve resistance, and thereby maintains an approximately constant flow rate through the valve device without requiring any power.

FIG. 3J shows an actuator 333 that can regulate the upstream pressure in the catheter 102. Similar to the actuator 330 shown in FIG. 3I, the actuator 333 includes the actuator contacts 335 and the lever arm 331. However, the lever arm 331 shown in FIG. 3J is bent or otherwise twisted such that the actuator contacts 335 act on opposing sides of the catheter 102. The desired upstream pressure can be obtained by manipulating the relative lengths and areas of the lever arms 331 and the actuator contacts 335. As shown in FIG. 3J, when the upstream pressure increases, the force on the first actuator contact 335a increases. The lever arm 331 transmits the force to the second actuator contact 335b such that it removes force from the catheter 102. This increases the opening of the catheter 102, and thus decreases the valve resistance to relieve the pressure buildup. In selected embodiments, the actuators 330 and 333 shown in FIGS. 3I and 3J can also be configured to prevent retrograde flow. In further embodiments, multiple interacting lever arms 331 and actuator contacts 335 can be combined to enhance flow and/or pressure control. Additionally, the mechanical actuators can be assisted by electrically-powered actuators to provide a more sophisticated control with lower power draw.

In other embodiments, other devices or methods that compress or otherwise constrict the catheter 102 and/or the reservoir 232 can be used to control flow rate. For example, the catheter 102 can be twisted incrementally about its longitudinal axis to create a variable resistance. As another example, the catheter 102 can be wound (e.g., either a partial turn or many turns) around a shaft or other solid object, and the catheter 102 can then be stretched to create tension that causes variable flow through the catheter 102. The catheter 102 can also be turned back on itself varying degrees to form one or more pinch points that can incrementally adjust flow rate. This actuation method can be advantageous because it can provide a level of passive activation, requires low force to vary the flow therein, and thus has a low power requirement.

Figure 4A:
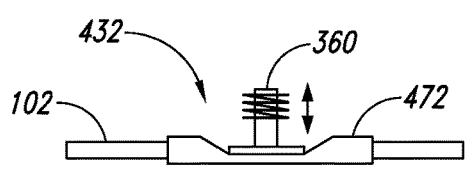
FIGS. 4A and 4B are side and perspective views, respectively, of reservoirs for a body fluid drainage system in accordance with embodiments of the present technology.
Figure 4B:
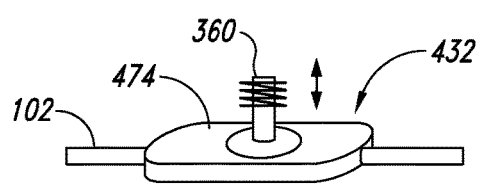

FIGS. 4A and 4B are side and perspective views, respectively, of reservoirs 432 for a body fluid drainage system (e.g., the drainage systems 100 and 150 shown in FIGS. 1A and 1B) in accordance with embodiments of the present technology. As shown in FIG. 4A, the reservoir 432 can include a tubular body 472 that has a larger cross-sectional area than the catheter 102 to which it connects. The tubular body 472 can be formed integrally with the catheter, and can therefore include the same material as the catheter 102. In other embodiments, the tubular body 472 can include materials that are different from those of the catheter 102. For example, the tubular body 472 can include a compliant material that is too elastic for the entire length of the catheter 102, but can advantageously expand to hold a desired volume of the body fluid within the reservoir 232.

As shown in FIG. 4B, the reservoir 432 includes a chamber 474. The chamber 474 shown in FIG. 4B has a generally flat, rectangular shape, but can have other suitable shape (e.g., spherical, cylindrical) for the reservoir 424. In selected embodiments, the chamber 474 can include a less compliant material than the catheter 102, but can also include one or more compliant regions that can be compressed by the actuator 360. In other embodiments, the reservoir 432 can have other suitable configurations that can contain a greater cross-sectional volume than the catheter 102.

Figure 5A:
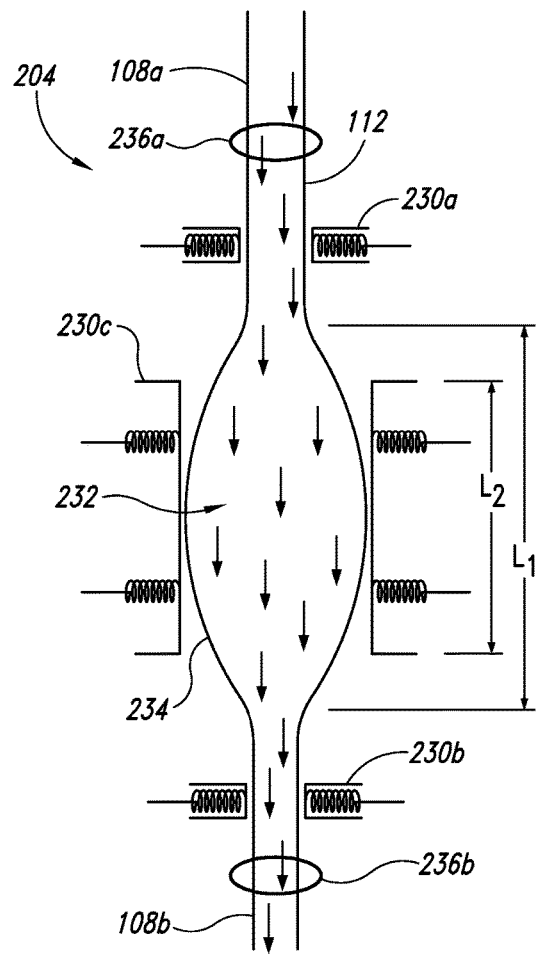
FIG. 5A is a schematic, cross-sectional top plan view of unobstructed antegrade flow through a valve device of a body fluid drainage system in accordance with an embodiment of the present technology.
Figure 5B:
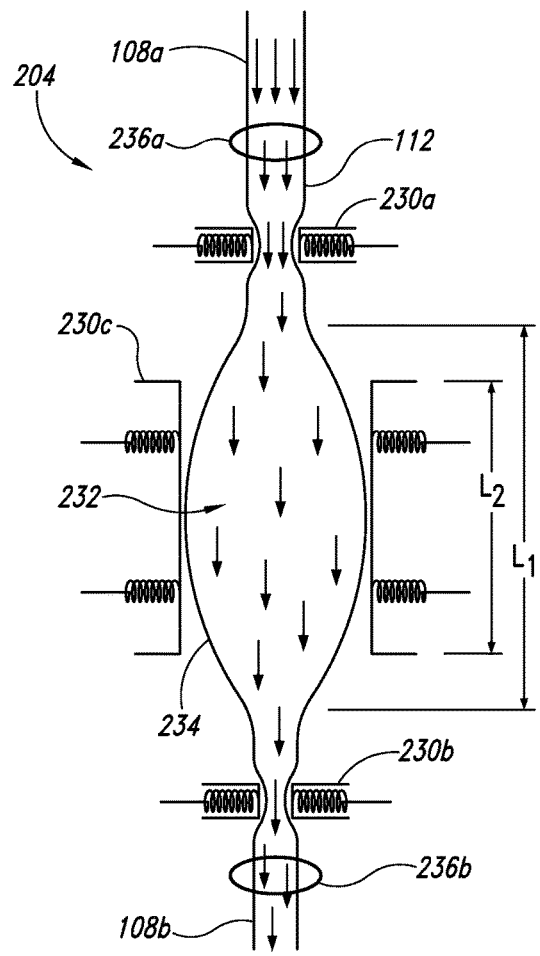
FIG. 5B is a schematic, cross-sectional top plan view of partially obstructed antegrade flow through the valve device of FIG. 5A.

FIGS. 5A-5D are schematic, cross-sectional top plan views of body fluid flow through the valve device 204 of FIG. 2B in accordance with an embodiment of the present technology. FIG. 5A, for example, shows the valve device 204 with all actuators 230 in an open position to provide unobstructed antegrade flow through a valve device 204. As shown in FIG. 5B, select actuators 230 can apply force against the exterior surface 112 of the catheter 102 to slow the flow rate of the body flow. More specifically, FIG. 5B shows the first actuator 230a in an intermediate position (i.e., between fully open and fully closed) that partially obstructs antegrade flow through the proximal portion 108a of the catheter 102. The second actuator 230b is also in an intermediate position, but applies a greater force to the exterior surface 112 of the catheter 102. Partially closed actuators 230 can be of particular advantage to prevent siphoning of the body fluid. Any adjustment (e.g., partially closed, closed, or open) of the actuators 230 can occur successively or in tandem.

Figure 5C:
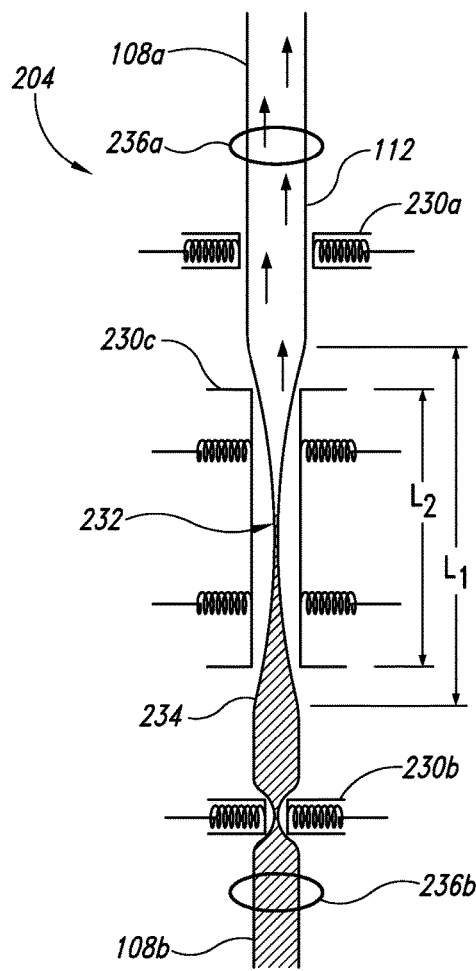
FIG. 5C is a schematic, cross-sectional top plan view of retrograde flow through the valve device of FIG. 5A.

The valve device 204 can also adjust to force antegrade flow and retrograde flow to "flush" the catheter 102 with the body fluid. As shown in FIG. 5C, for example, the second actuator 230b can be closed to stop fluid flow through the distal portion 108b of the catheter 102, and the third actuator 230c can compress the reservoir 232 to evacuate the body fluid collected therein. This forces the body fluid through the open first actuator 230a into the proximal portion 108a of the catheter 102, and thereby clears obstructions and loosens build up of blood, cellular debris, postoperative debris, and/or other debris within in the proximal portion 108a and/or the inlet region of the catheter 102.

Figure 5D:
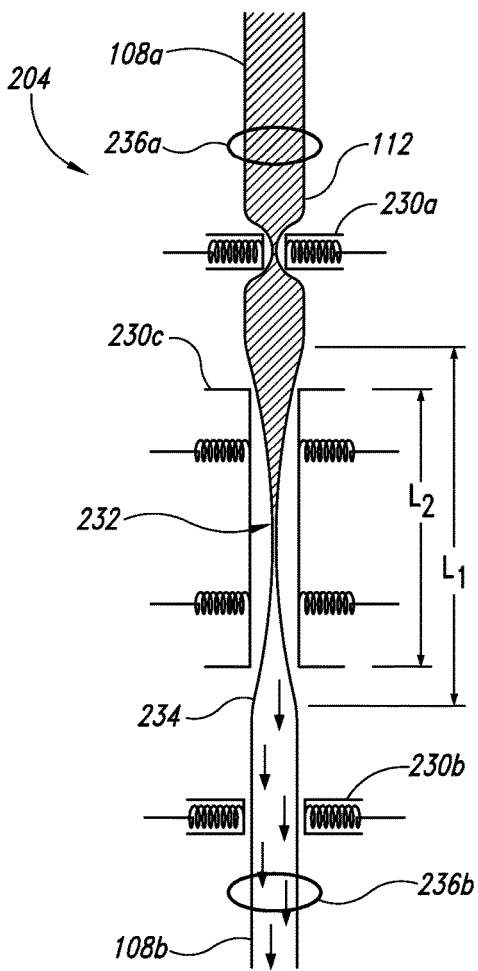
FIG. 5D is a schematic, cross-sectional top plan view of forced antegrade flow through the valve device of FIG. 5A.

Similar to the backflushing shown in FIG. 5C, the valve device 204 can also adjust to provide a forward flush. For example, as shown in FIG. 5D, the first actuator 230a can close to stop fluid flow above it, and the third actuator 230c can compress the reservoir 232 to force the body fluid through the distal portion 108b of the catheter 102. This forced flow provided to either the proximal or distal portions 108a-b of the catheter 102 can dislodge obstructions (e.g., blood, cellular debris, postoperative debris) in the catheter 102 and disrupt tissue invasion that may occur at the inlet or outlet regions (not shown) of the catheter 102.

In selected embodiments, the valve device 104 can perform periodic backflushing and forward flushing to reduce the likelihood of obstructions. The periodic forced flow can also be used in conjunction with the diagnostic tests described above. In other embodiments, the backflushing and/or forward flushing can be performed manually by the patient or caregiver by pressing on the reservoir 232 and directing the body fluid in the desired direction.

Figure 6A:
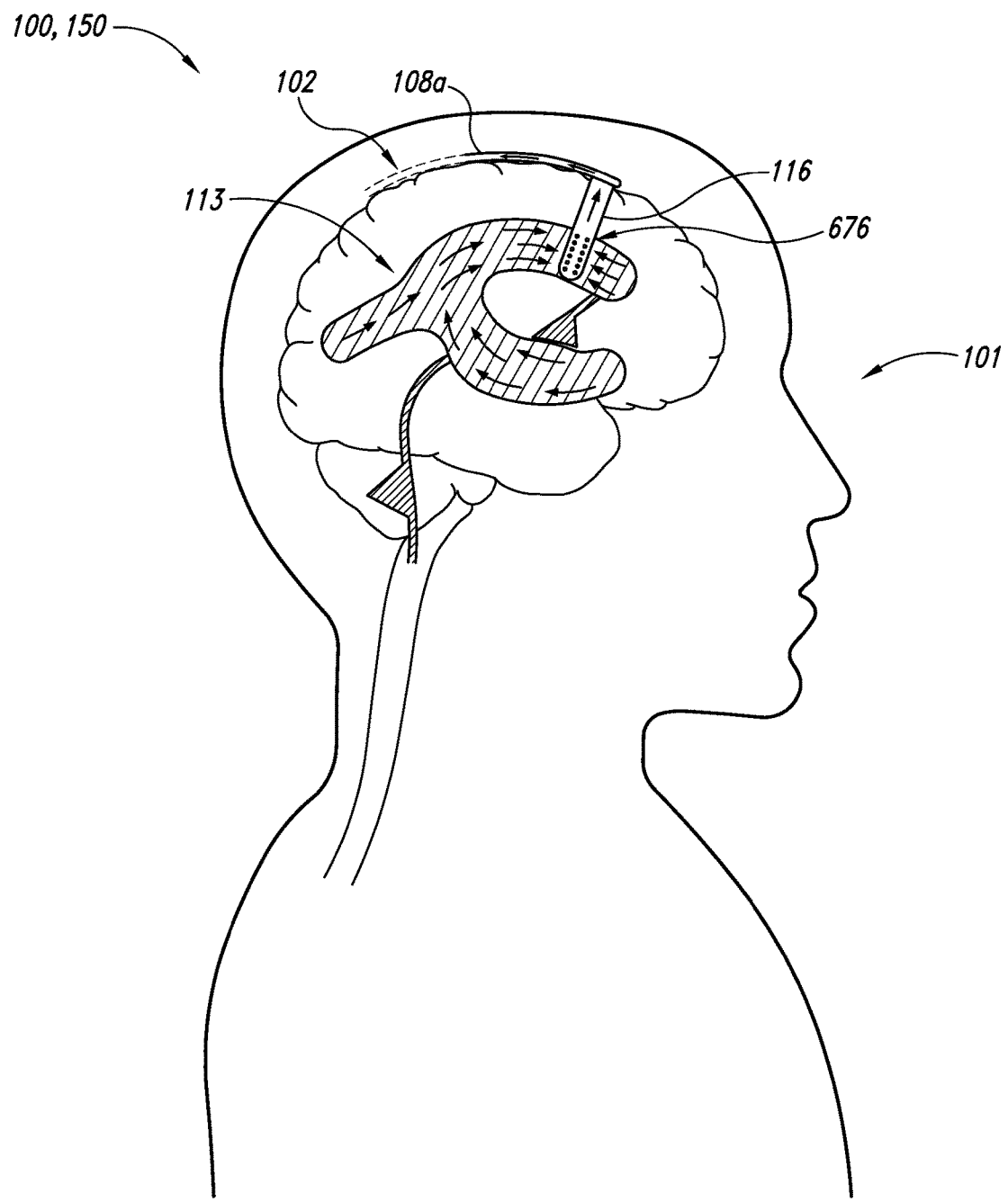
FIG. 6A is a schematic, cross-sectional side view of antegrade flow through a body fluid drainage system implanted in a ventricle in accordance with an embodiment of the present technology.
Figure 6B:
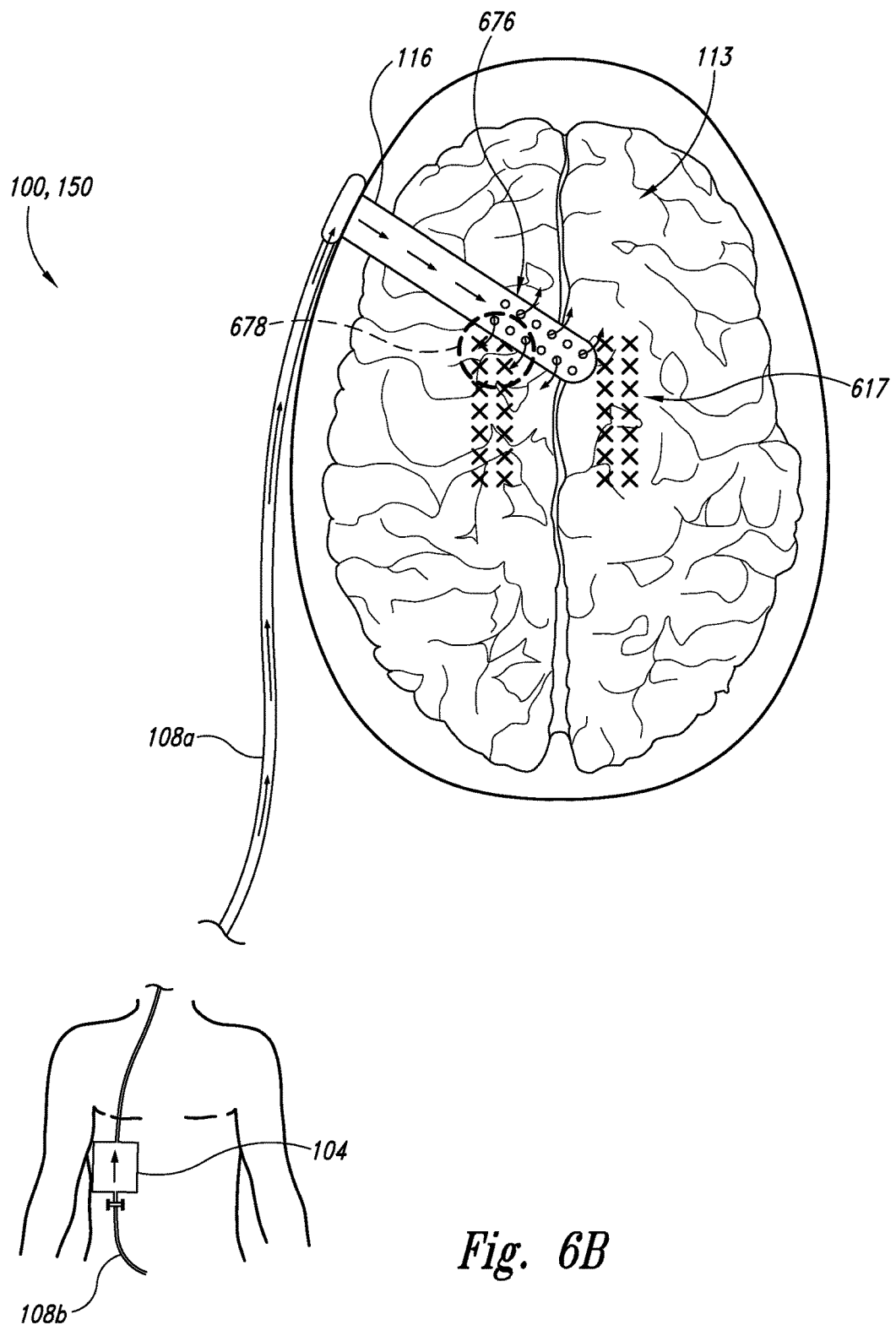
FIG. 6B is a schematic, cross-sectional top view of retrograde flow through the body fluid drainage system of FIG. 6A.

FIGS. 6A and 6B are illustrations of antegrade flow and retrograde flow, respectively, through the inlet region 116 of the body fluid drainage systems 100 and 150 of FIGS. 1A and 1B described above in accordance with an embodiment of the present technology. In the illustrated embodiment, the inlet region 116 is inserted into the lateral ventricle 113 such that the drainage systems 100 and 150 can remove excess CSF fluid. As shown in FIG. 6A, the inlet region 116 of the catheter 102 can include a plurality of openings 676 through which excess CSF can enter the drainage systems 100 and 150. As shown in FIG. 6B, the CSF can be directed in retrograde flow via the valve device 104. For example, the valve device 104 can be configured as shown in FIG. 5C to force flow through the proximal portion 108a of the catheter 102. This can expel CSF out of the openings 676 and clear the inlet region 116 of obstructions. For example, as shown in FIG. 6B, the inlet region 116 can be obstructed with choroid plexus ingrowth, ependymal lining ingrowth, and/or other tissue ingrowth 617. The forced retrograde flow of CSF can mobilize an ingrown portion 678 such that it no longer blocks the openings 676 of the inlet region 116. In other embodiments, the valve device 104 can force antegrade flow through the distal portion 108b of the catheter to reduce the likelihood of tissue ingrowth or other obstructions at the outlet region 118 (not shown) of the catheter 102.

Figure 7A:
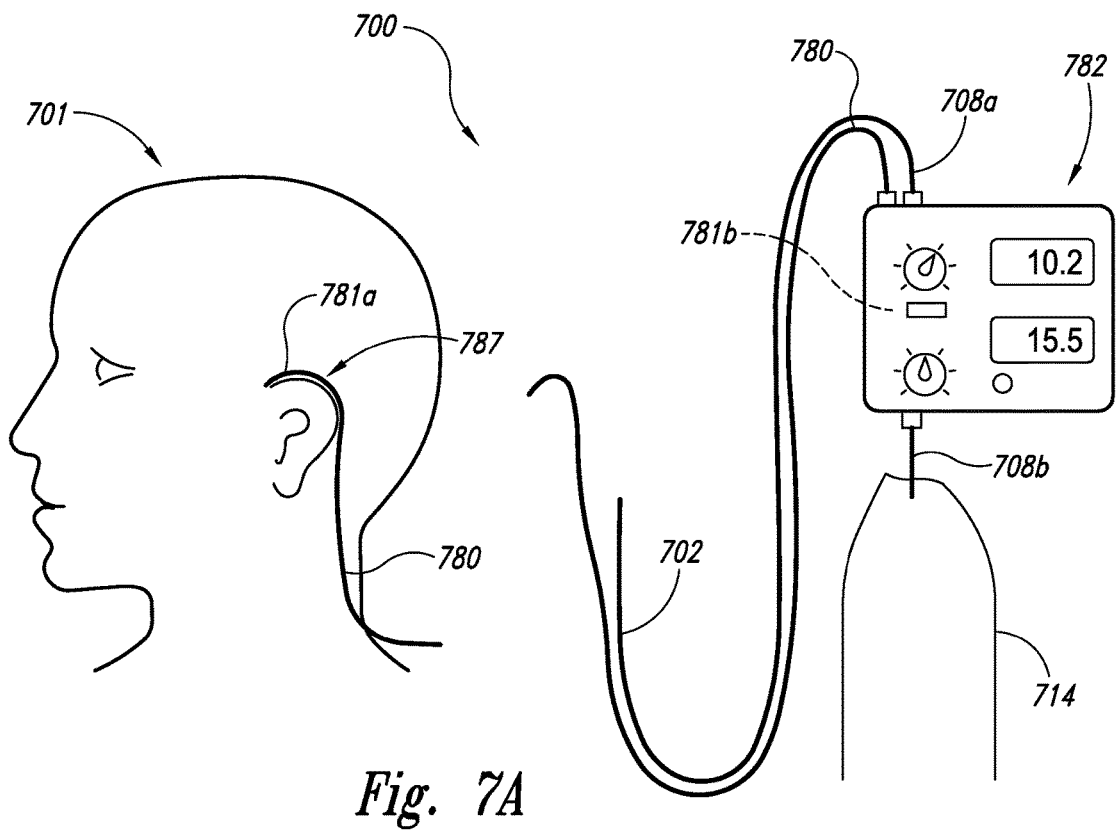
FIG. 7A is a partial schematic view of a body fluid drainage system in accordance with a further embodiment of the present technology.
Figure 7B:
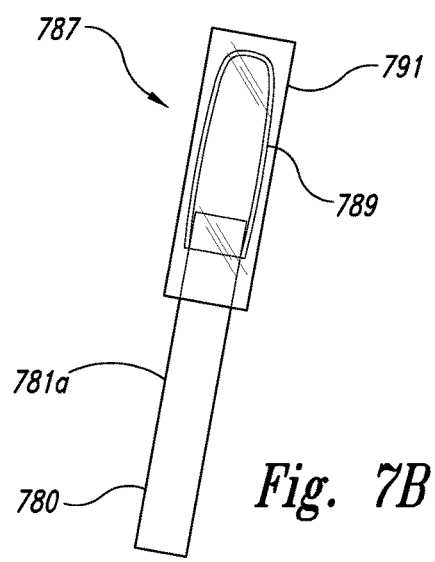
FIGS. 7B-7D are schematic views of portions of the body fluid drainage system of FIG. 7A.
Figure 7C:
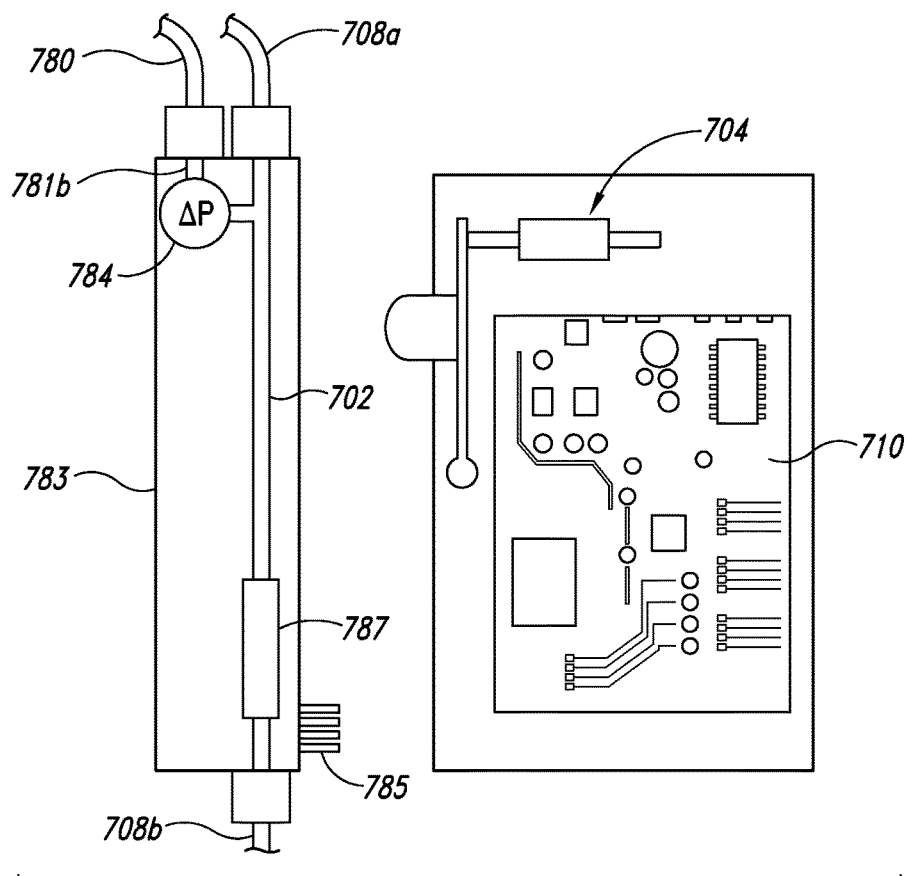
Figure 7D:
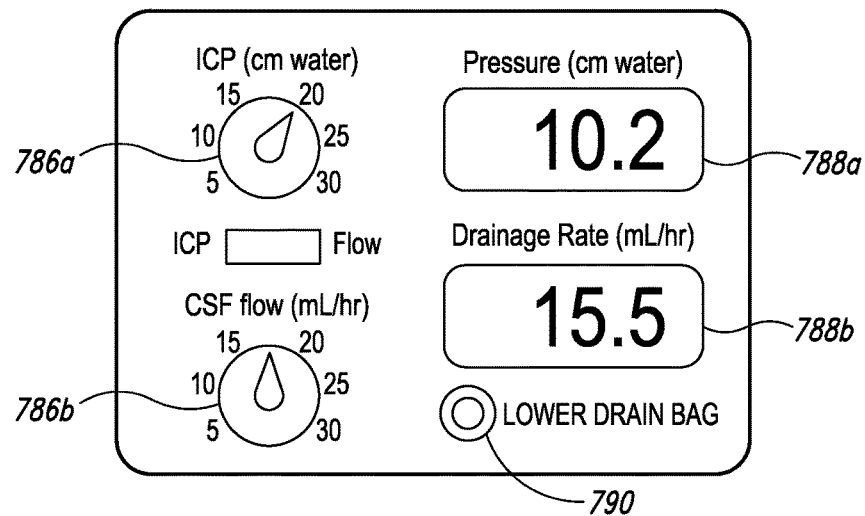

FIG. 7A is a partial schematic view of a body fluid drainage system 700 ("drainage system 700") in accordance with a further embodiment of the present technology, and FIGS. 7B-7D show enlarged portions of the drainage system 700 of FIG. 7A. The drainage system 700 can include features generally similar to the external drainage system 150 described above with reference to FIG. 1B. For example, the drainage system 700 can include a catheter 702 that has a proximal portion 708a at the source of excess body fluid and a distal portion 708b that drains the excess body fluid to an external receptacle 714. In other embodiments, the drainage system 700 can discharge the excess body fluid to an internal receptacle, such as described above with reference to FIG. 1A. As shown in FIG. 7C, the drainage system 700 can also include a valve device 704 that applies forces to the exterior of the catheter 102 to regulate the drainage of the body fluid.

As shown in FIG. 7A, the drainage system 700 further includes a pressure reference line 780 ("reference line") and a controller interface 782. Both can be coupled to a controller 710 (FIG. 7C) that has generally similar features as the controller 110 described above. The reference line 780 can include a fluid-filled tube that extends between a flexible end cap 787 at a first end portion 781a and a pressure sensor 784 at the second end portion 781b. In a CSF drainage system, the fluid that fills the reference line 780 can be a silicone oil or other fluid that has a density substantially equal to CSF. In other embodiments, the reference line 780 can include a fluid that has a density substantially equal to the body fluid being drained. In further embodiments, the reference line 780 can be filled with a fluid that has a density different from the body fluid being drained, and the differing densities can be accounted for in an associated algorithm.

As shown in FIG. 7B, the end cap 787 can include a flexible silicone balloon, bag, and/or other flexible structure 789 and a protective cage or barrier 791. The barrier 791 can prevent accidental compression of the flexible structure 789 and can be vented to allow pressure communication with the environment external to the barrier 791. For an implantable device, the barrier 791 can be designed to prevent body tissue from interacting with the flexible structure 789. In one embodiment, the end cap 787 has a diameter of a few millimeters and a length of approximately 1 cm to discretely fit over the patient's ear as shown in FIG. 7A. In other embodiments, the end cap 787 can have larger or smaller dimensions to accommodate its placement.

To obtain a desired pressure, the end cap 787 can be positioned proximate to the desired pressure measurement, and the pressure sensor 784 can be placed in fluid communication with the catheter 702 (i.e., the drain line). For example, in the illustrated embodiment, the end cap 787 is mounted proximate to the Foramen of Monroe to measure ICP, and the pressure sensor 784 is placed in fluid communication with the catheter 702. The difference between the pressure in the reference line 780 and the pressure of the catheter 702A can be determined using a differential pressure sensor and/or two independent pressure sensors. This differential pressure measurement incorporates a direct measurement of the pressure head caused by the body fluid in the catheter 702. Thus, the differential pressure measurement is equal to the pressure of the drainage system 700 at the end cap 787 (e.g., ICP). Advantageously, this direct measurement of the pressure head allows the reference line 780 to automatically compensate for positional changes of the pressure sensor 784 and the valve device 704 to which it is coupled. Therefore, the drainage system 700 can derive an accurate pressure measurement regardless of movement of the patient 701 and/or the valve device 704. Accordingly, the drainage system 700 measures ICP more accurately than conventional CSF drainage systems that require the patient 701 to remain motionless during drainage procedures.

As shown in FIG. 7C, the proximal portion 708a of the catheter 702 and the second end portion 781b of the pressure reference line 780 can extend into a cartridge 783. The cartridge 783 can also house the pressure sensor 784 of the pressure reference line 780, a flow rate sensor 784, and/or other pressure and flow rate sensors (not shown) that contact CSF or other body fluids. In other embodiments, the pressure sensors and flow sensors can measure pressure and flow rate through the wall of the catheter 702 such that they do not contact the body fluid. Additionally, as shown in FIG. 7C, the cartridge 783 can also include an electrical connection 785 that couples the drainage system 700 to a power source (not shown).

In selected embodiments, the cartridge 783 is disposable such that it can be coupled to reusable portions of the drainage system 700 that do not contact the body fluid. For example, as shown in FIG. 7C, the disposable cartridge 783 can be coupled with the controller 710 and the valve device 704. In selected embodiments, the disposable cartridge 783, the reusable controller 710, and/or other reusable components can be designed with registration features and positive engagement mechanisms such that they can only be assembled with the proper geometry. As such, the portions of the drainage system 700 that are contaminated with body fluid (i.e., the portions stored within the cartridge 783) can be thrown out after use, while the controller 710, the valve device 704, and other more intricate devices (e.g., flow sensors) can be conserved and used with a plurality of disposable cartridges 783.

FIG. 7D shows of the controller interface 782 of the drainage system 700 of FIG. 7A. The controller interface 782 can include one or more user controls 786 (identified individually as a first user control 786a and a second user control 786b) and displays (identified individually as a first display 788a and a second display 788b), both operatively coupled to the controller 710. The user controls 786 can allow a user (e.g., a medical professional) to select and adjust the desired condition for pressure or flow rate, as well as the tolerances of the drainage system 700. For example, as shown in FIG. 7D, the user controls 786 can change the desired ICP and/or flow rate of the drainage system 700. The user controls 786 can be coupled to the controller 710 such that the controller 710 can adjust the valve device 704 to output the selected ICP or flow rate. The displays 788 can show the actual measured ICP and drainage rate to ensure the drainage system 700 meets the selected tolerances. Additionally, as shown in FIG. 7D, the controller interface 782 can also include a warning signal 790 (e.g., a light, a bell) that activates when conditions do not allow proper drainage. For example, the warning signal 790 can be a light that illuminates when the external receptacle 714 is positioned too high relative to the rest of the drainage system 700.

Figure 8A:
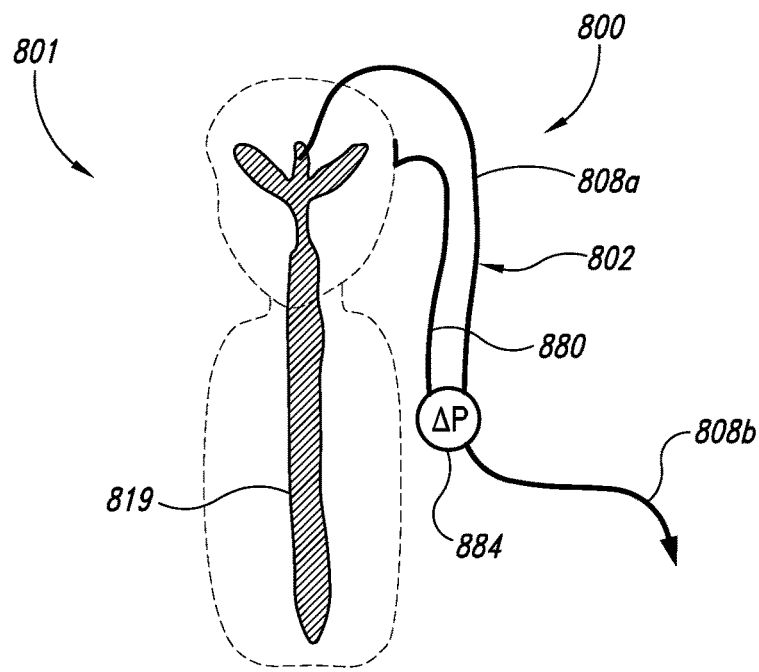
FIGS. 8A and 8B are schematic views of external body fluid drainage systems installed in different portions of a CSF system in accordance with additional embodiments of the present technology.
Figure 8B:
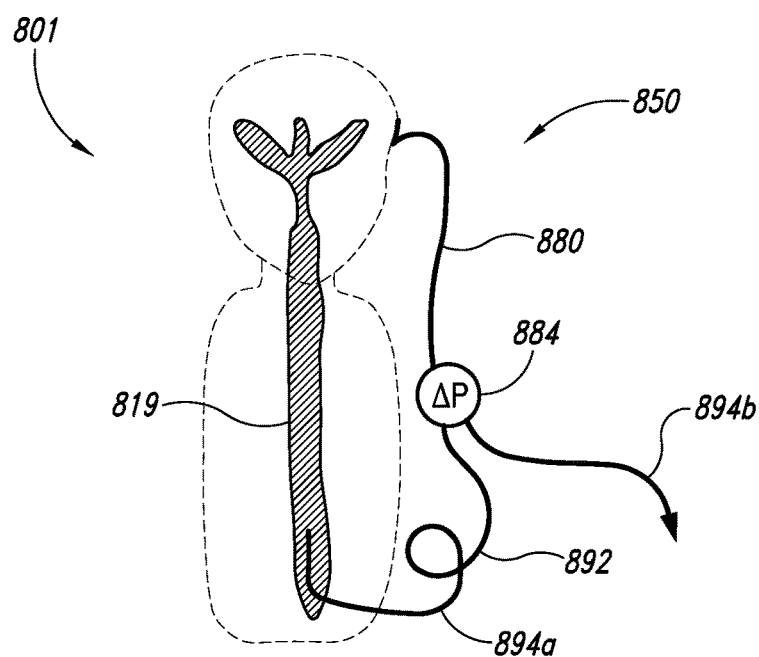

FIGS. 8A and 8B are schematic views of body fluid drainage systems 800 and 850 installed in a CSF system 819 in accordance with additional embodiments of the present technology. The body fluid drainage systems 800 and 850 can include generally similar features as the drainage system 700 described above with reference to FIGS. 7A-7D. For example, the body fluid drainage systems 800 and 850 include a pressure reference line 880 mounted over the equivalent external location of the Foramen Monroe to automatically account for movement of a patient 801 and/or an external receptacle (not shown).

As shown in FIGS. 8A and 8B, the drainage systems 800 and 850 can drain CSF from different portions of the CSF system 819. For example, in the embodiment illustrated in FIG. 8A, the body fluid drainage system 800 includes a catheter 802 that has a proximal portion 808a inserted into the upper portion (e.g., a ventricle) of the CSF system 819. Similar to the drainage systems 100, 150, and 700 shown in FIGS. 1A, 1B, and 7A-7D, the cranially inserted body fluid drainage system 800 can drain fluid through a distal portion 808b of the catheter 102 to an external receptacle or internal cavity.

The body fluid drainage system 850 shown in FIG. 8B includes a catheter 892 inserted into the patient's lumbar region the lower portion of the CSF system 819. Similar to the cranially inserted drainage system 800 described above, the body fluid drainage system 850 can drain body fluid (e.g., CSF) from a proximal portion 894a of the catheter 892 to a distal portion 894b that is in fluid communication with an external receptacle or internal reabsorbtion cavity. Advantageously, despite the different insertion points of the body fluid drainage systems 800 and 850, the pressure reference line 880 can still adjust for movement of the patient 801 to allow for accurate ICP measurements.

From the foregoing, it will be appreciated that specific embodiments of the present technology have been described herein for purposes of illustration, but that various modifications may be made without deviating from the spirit and scope of the disclosure. For example, the pressure reference lines 780 and 880 shown in FIGS. 7A-8B can be added to the body fluid drainage systems 100 and 150 shown in FIGS. 1A and 1B. Additionally, the pressure reference lines 780 and 880 can be implanted in a patient, rather than externally mounted as in FIGS. 7A-8B. Aspects of the disclosure described in the context of particular embodiments may be combined or eliminated in other embodiments. For example, the valve device 104 shown in FIG. 2A can include additional actuators that control body fluid flow through the catheter 102. Further, while advantages associated with certain embodiments of the disclosure have been described in the context of those embodiments, other embodiments may also exhibit such advantages, and not all embodiments need necessarily exhibit such advantages to fall within the scope of the disclosure. Accordingly, embodiments of the disclosure are not limited except as by the appended claims.

We claim:

1. A body fluid drainage system, comprising:
    a catheter having a proximal portion and a distal portion opposite the proximal portion, wherein the proximal portion includes an inlet configured to be implanted into a patient and in fluid communication with a site of excess body fluid within the patient;
    a pressure sensor spaced apart from the site of excess body fluid, wherein the pressure sensor is configured to measure pressure within the catheter;
    a reference line comprising
        a tube having a first end portion and a second end portion opposite the first end portion;
        an end cap at the first end portion, wherein the end cap is configured to be positioned at least proximate to the site of excess body fluid and external to the site of excess body fluid; and
        a reference fluid in the tube, the reference fluid having a predetermined density, wherein the reference line is configured to provide a pressure head between the site of excess body fluid and the pressure sensor; and
    a controller operatively coupled to the pressure sensor and the reference line, wherein the controller is configured to derive pressure in the site of excess body fluid via the pressure sensor and the reference line.

2. The body fluid drainage system of claim 1 wherein the pressure sensor is operably coupled to the catheter and the second end portion of the tube, and wherein the pressure sensor is configured to measure differential pressure between the tube and the catheter.

3. The body fluid drainage system of claim 1 wherein the pressure sensor is a first pressure sensor operably coupled to the catheter, and wherein the body fluid drainage system further comprises:
    a second pressure sensor operably coupled to the second end portion of the tube, wherein the second pressure sensor is configured to measure pressure in the tube, and
    wherein the controller is configured to use the measured pressures of the first and second sensors to derive the pressure in the site of excess body fluid.

4. The body fluid drainage system of claim 1, further comprising a valve device configured to change resistance to flow through the catheter, wherein the controller is configured to change the resistance to flow in response to the derived pressure in the site of excess body fluid.

5. The body fluid drainage system of claim 1, further comprising:
    a reservoir between the proximal and distal portions of the catheter, the reservoir having a cross-sectional dimension greater than a cross-sectional dimension of the proximal and distal portions of the catheter, wherein the reservoir is configured to be compressed to flush fluid at least one of proximally or distally through the catheter.

6. The body fluid drainage system of claim 5, further comprising:
    an actuator at an exterior surface of the reservoir, wherein the actuator is configured to be movable between at least an open position and a closed position.

7. The body fluid drainage system of claim 6 wherein the actuator is a first actuator, and wherein the body fluid drainage system further comprises:
    a second actuator acting on an external surface of the catheter, wherein the controller is configured to change the position of the first and second actuators independently of one another.

8. The body fluid drainage system of claim 1, further comprising a valve device configured to change resistance to flow through the catheter, wherein the valve device comprises at least one pinch valve.

9. The body fluid drainage system of claim 1, further comprising: a magnetic shield over the controller, the magnetic shield obstructing magnetic interference with the controller.

10. The body fluid drainage system of claim 1, further comprising a valve device having an actuator acting on the catheter, and wherein the catheter comprises peristaltic pump tubing proximate to the actuator.

11. The body fluid drainage system of claim 1, further comprising:
    a reservoir between the proximal and distal portions of the catheter, the reservoir having a cross-sectional dimension greater than a cross-sectional dimension of the catheter, wherein the reservoir has a first length; and
    an actuator over an exterior surface of the reservoir, the actuator having a second length at least equal to the first length such that the actuator compresses the reservoir along the first length.

12. The body fluid drainage system of claim 1, further comprising at least one of an accelerometer or an inclinometer.

13. A body fluid drainage system, comprising:
    a catheter having a proximal portion and a distal portion opposite the proximal portion, wherein the proximal portion includes an inlet configured to be implanted into a patient and in fluid communication with a site of excess body fluid within the patient;
    a pressure sensor spaced apart from the site of excess body fluid, wherein the pressure sensor is configured to measure pressure within the catheter;

a reference line comprising
a tube having a first end portion and a second end portion opposite the first end portion, wherein the tube is configured to be at least partially filled with a liquid; and
an end cap at the first end portion, wherein the end cap is configured to be positioned proximate to the site of excess body fluid,
wherein the reference line is configured to provide a pressure head between the site of excess body fluid and the pressure sensor; and
a controller operatively coupled to the pressure sensor and the reference line, wherein the controller is configured to derive pressure in the site of excess body fluid via the pressure sensor and the reference line.

14. The body fluid drainage system of claim 13 wherein the pressure sensor is operably coupled to the catheter and the second end portion of the tube, and wherein the pressure sensor is configured to measure differential pressure between the tube and the catheter.

15. The body fluid drainage system of claim 13 wherein the pressure sensor is a first pressure sensor operably coupled to the catheter, and wherein the body fluid drainage system further comprises:
a second pressure sensor operably coupled to the second end portion of the tube, wherein the second pressure sensor is configured to measure pressure in the tube, and
wherein the controller is configured to use the measured pressures of the first and second sensors to derive the pressure in the site of excess body fluid.

16. The body fluid drainage system of claim 13, further comprising a valve device configured to change resistance to flow through the catheter, wherein the controller is configured to change the resistance to flow in response to the derived pressure in the site of excess body fluid.

17. The body fluid drainage system of claim 13, further comprising:
a reservoir between the proximal and distal portions of the catheter, the reservoir having a cross-sectional dimension greater than a cross-sectional dimension of the proximal and distal portions of the catheter, wherein the reservoir is configured to be compressed to flush fluid at least one of proximally or distally through the catheter.

18. The body fluid drainage system of claim 17, further comprising:
an actuator at an exterior surface of the reservoir, wherein the actuator is configured to be movable between at least an open position and a closed position.

19. The body fluid drainage system of claim 18 wherein the actuator is a first actuator, and wherein the body fluid drainage system further comprises:
a second actuator acting on an external surface of the catheter, wherein the controller is configured to change the position of the first and second actuators independently of one another.

20. The body fluid drainage system of claim 13, further comprising a valve device configured to change resistance to flow through the catheter, wherein the valve device comprises at least one pinch valve.

21. The body fluid drainage system of claim 13, further comprising: a magnetic shield over the controller, the magnetic shield obstructing magnetic interference with the controller.

22. The body fluid drainage system of claim 13, further comprising a valve device having an actuator acting on the catheter, and wherein the catheter comprises peristaltic pump tubing proximate to the actuator.

23. The body fluid drainage system of claim 13, further comprising:
a reservoir between the proximal and distal portions of the catheter, the reservoir having a cross-sectional dimension greater than a cross-sectional dimension of the catheter, wherein the reservoir has a first length; and
an actuator over an exterior surface of the reservoir, the actuator having a second length at least equal to the first length such that the actuator compresses the reservoir along the first length.

24. The body fluid drainage system of claim 13, further comprising at least one of an accelerometer or an inclinometer.

25. The body fluid drainage system of claim 1 wherein the inlet is configured to be implanted into a ventricle of a patient's brain.

26. The body fluid drainage system of claim 1 wherein the controller is configured to derive intracranial pressure.

27. The body fluid drainage system of claim 1 wherein the inlet is configured to be inserted into a patient's lumbar region.

28. The body fluid drainage system of claim 1 wherein the reference line is configured to be mounted over an external location of a patient's foramen of Monro.

29. The body fluid drainage system of claim 1 wherein the reference line is configured to be implanted in the patient.

30. The body fluid drainage system of claim 1 wherein the end cap is configured to fit over a patient's ear.

31. The body fluid drainage system of claim 1, further comprising a flow rate sensor configured to measure flow rate within the catheter.

32. The body fluid drainage system of claim 1, further comprising a cartridge housing having portions that contact the excess body fluid.

33. The body fluid drainage system of claim 1, further comprising a controller interface operatively coupled to the controller, wherein the controller interface includes one or more user controls and displays configured to allow a user to select and adjust one or more desired conditions.

34. The body fluid drainage system of claim 13 wherein the inlet is configured to be implanted into a ventricle of a patient's brain.

35. The body fluid drainage system of claim 13 wherein the controller is configured to derive intracranial pressure.

36. The body fluid drainage system of claim 13 wherein the inlet is configured to be inserted into a patient's lumbar region.

37. The body fluid drainage system of claim 13 wherein the reference line is configured to be mounted over an external location of a patient's foramen of Monro.

38. The body fluid drainage system of claim 13 wherein the reference line is configured to be implanted in the patient.

39. The body fluid drainage system of claim 13 wherein the liquid at least partially filling the tube has a density equal to a density of the excess body fluid.

40. The body fluid drainage system of claim 13 wherein the liquid at least partially filling the tube has a density different from a density of the excess body fluid.

41. The body fluid drainage system of claim 13 wherein the end cap includes a flexible structure and a protective barrier configured to inhibit compression of the flexible structure.

42. The body fluid drainage system of claim 13 wherein the end cap is configured to fit over a patient's ear.

43. The body fluid drainage system of claim 13, further comprising a flow rate sensor configured to measure flow rate within the catheter.

44. The body fluid drainage system of claim 13, further comprising a cartridge housing having portions configured to contact the excess body fluid.

45. The body fluid drainage system of claim 13, further comprising a controller interface operatively coupled to the controller, wherein the controller interface includes one or more user controls and displays configured to allow a user to select and adjust one or more desired conditions.

\* \* \* \* \*